(12) United States Patent
Hochman

(10) Patent No.: US 10,946,139 B2
(45) Date of Patent: Mar. 16, 2021

(54) DISPOSABLE ASSEMBLY FOR DRUG INFUSION WITH PRESSURE SENSING FOR IDENTIFICATION OF AND INJECTION INTO FLUID-FILLED ANATOMIC SPACES

(71) Applicant: Milestone Scientific, Inc., Livingston, NJ (US)

(72) Inventor: Mark N. Hochman, Great Neck, NY (US)

(73) Assignee: MILESTONE SCIENTIFIC, INC., Roseland, NJ (US)

( * ) Notice: Subject to any disclaimer, the term of this patent is extended or adjusted under 35 U.S.C. 154(b) by 515 days.

(21) Appl. No.: 15/796,439

(22) Filed: Oct. 27, 2017

(65) Prior Publication Data

US 2018/0064870 A1 Mar. 8, 2018

Related U.S. Application Data

(63) Continuation of application No. 13/540,880, filed on Jul. 3, 2012, now Pat. No. 9,956,341.

(51) Int. Cl.
*A61M 5/168* (2006.01)
*G16H 20/17* (2018.01)
(Continued)

(52) U.S. Cl.
CPC ............ *A61M 5/168* (2013.01); *G16H 20/17* (2018.01); *A61B 5/032* (2013.01); *A61F 9/0008* (2013.01);
(Continued)

(58) Field of Classification Search
CPC .................. A61M 5/168; A61M 5/178; A61M 2005/1588; A61M 2205/6045;
(Continued)

(56) References Cited

U.S. PATENT DOCUMENTS 3,867,934 A 2/1975 Ollivier
4,356,826 A 11/1982 Kubota
(Continued)

FOREIGN PATENT DOCUMENTS

DE 20 2005 019430 2/2006
EP 0303824 2/1989
(Continued)

OTHER PUBLICATIONS

Ghelber, Oscar, et al., "Ident. of the Epidural Space Using Pressure Measurement . . . ", Regional Anesthesia and Pain Medicine, vol. 33, No. 4 Jul.-Aug. 2008, pp. 346-352.
(Continued)

*Primary Examiner* — Lauren P Farrar
(74) *Attorney, Agent, or Firm* — Niels Haun; Dann, Dorfman, Herrell & Skillman, P.C.

(57) ABSTRACT

A disposable fluid flow assembly for operation in connection with a fluid pump configured to provide a flow of fluid to the disposable fluid flow assembly is provided. The disposable fluid flow assembly includes an elongated flexible tube, a needle hub connected with the flexible tube, a pressure sensor for sensing fluid pressure, and an identification circuit embedded connected with the pressure sensor. The identification is configured to provide a plurality of signals to the central controller of the fluid pump when the disposable needle assembly is connected with the fluid pump. The plurality of signals may include various signals, such as a signal to identify physical characteristics of the assembly, a signal to ensure that the assembly is authentic, a signal to ensure that the disposable assembly is not re-used, and/or a signal to ensure that the pressure signal is connected and operating properly.

32 Claims, 11 Drawing Sheets

(51) Int. Cl.
*A61M 19/00* (2006.01)
*A61F 9/00* (2006.01)
*A61B 5/03* (2006.01)
*A61M 5/178* (2006.01)
*A61M 5/158* (2006.01)

(52) U.S. Cl.
CPC .......... *A61M 5/178* (2013.01); *A61M 19/00* (2013.01); *A61M 2005/1588* (2013.01); *A61M 2205/581* (2013.01); *A61M 2205/583* (2013.01); *A61M 2205/6018* (2013.01); *A61M 2205/6045* (2013.01)

(58) Field of Classification Search
CPC .... A61M 2205/6018; A61M 2205/581; A61M 2205/583; A61M 19/00; A61M 2205/52; A61M 5/00; A61M 31/00; A61B 5/032; G16H 20/17; A61F 9/0008
See application file for complete search history.

(56) References Cited

U.S. PATENT DOCUMENTS

| | | | |
|---|---|---|---|
| 4,403,988 A | 9/1983 | Binard | |
| 4,518,383 A | 5/1985 | Evans et al. | |
| 4,624,659 A | 11/1986 | Goldberg | |
| 4,679,567 A | 7/1987 | Hanlon | |
| 4,790,821 A | 12/1988 | Stines | |
| 4,801,293 A | 1/1989 | Jackson | |
| 4,893,630 A | 1/1990 | Bray, Jr. | |
| 4,988,337 A | 1/1991 | Ito | |
| 4,998,914 A | 3/1991 | Wiest | |
| 5,100,390 A | 3/1992 | Lubeck | |
| 5,178,603 A | 1/1993 | Prince | |
| 5,197,895 A * | 3/1993 | Stupecky | A61B 5/087 285/119 |
| 5,267,565 A | 12/1993 | Beard | |
| 5,269,762 A | 12/1993 | Armbruster | |
| 5,295,967 A | 3/1994 | Rondelet et al. | |
| D348,101 S | 6/1994 | Poli | |
| 5,378,231 A | 1/1995 | Johnson | |
| 5,405,269 A | 4/1995 | Stupecky | |
| D360,259 S | 7/1995 | Ijiri | |
| 5,520,650 A | 5/1996 | Zadini | |
| 5,611,778 A | 3/1997 | Brinon | |
| 5,660,567 A | 8/1997 | Nierlich et al. | |
| 5,681,285 A | 10/1997 | Ford | |
| 5,690,618 A | 11/1997 | Smith | |
| D390,654 S | 2/1998 | Alsberg | |
| 5,727,553 A | 3/1998 | Saad | |
| 5,810,770 A | 9/1998 | Chin | |
| D409,148 S | 5/1999 | Hirai | |
| 5,902,273 A | 5/1999 | Yang et al. | |
| 5,954,701 A | 9/1999 | Matalon | |
| 6,022,337 A | 2/2000 | Herbst | |
| 6,024,576 A | 2/2000 | Bevirt et al. | |
| 6,120,457 A | 9/2000 | Coombes | |
| 6,126,610 A * | 10/2000 | Rich | A61M 16/0816 600/529 |
| 6,159,161 A | 12/2000 | Hodosh | |
| D436,927 S | 1/2001 | Hogan | |
| 6,200,289 B1 | 3/2001 | Hochman et al. | |
| 6,468,241 B1 | 10/2002 | Gelfand et al. | |
| 6,569,147 B1 | 5/2003 | Evans | |
| 6,652,482 B2 | 11/2003 | Hochman | |
| 6,695,806 B2 | 2/2004 | Gelfand et al. | |
| 6,705,990 B1 | 3/2004 | Gallant | |
| 6,716,192 B1 | 4/2004 | Orosz, Jr. | |
| 6,773,417 B2 | 8/2004 | Fitzgibbons et al. | |
| 6,786,885 B2 | 9/2004 | Hochman | |
| 6,866,648 B2 | 3/2005 | Hadzic | |
| 6,886,648 B1 | 5/2005 | Hata | |
| 6,887,216 B2 | 5/2005 | Hochman | |
| 6,942,637 B2 | 9/2005 | Cartledge | |
| 7,022,072 B2 | 4/2006 | Fox | |
| 7,198,602 B2 | 4/2007 | Eide | |
| 7,285,100 B2 | 10/2007 | Lemaire | |
| D556,910 S | 12/2007 | Reihanifam | |
| 7,335,162 B2 | 2/2008 | Eide | |
| 7,364,570 B2 | 4/2008 | Gerondale | |
| 7,395,214 B2 | 7/2008 | Shillingburg | |
| 7,449,008 B2 | 11/2008 | Hochman | |
| D600,644 S | 9/2009 | Leung | |
| 7,604,602 B2 | 10/2009 | Roteliuk et al. | |
| 7,618,409 B2 | 11/2009 | Hochman | |
| 7,635,338 B2 | 12/2009 | Eide | |
| 7,641,637 B2 | 1/2010 | Gerondale | |
| 7,727,224 B2 | 6/2010 | Hadzic | |
| 7,775,985 B2 | 8/2010 | Eide | |
| D630,727 S | 1/2011 | Wittwer | |
| 7,896,833 B2 | 3/2011 | Hochman | |
| 7,922,689 B2 | 4/2011 | Lechner | |
| D642,984 S | 8/2011 | Arai | |
| 8,002,736 B2 | 8/2011 | Patrick | |
| 8,016,763 B2 | 9/2011 | Eide | |
| 8,079,976 B2 | 12/2011 | Patrick et al. | |
| 8,137,312 B2 | 3/2012 | Sundar et al. | |
| 8,142,414 B2 | 3/2012 | Patrick et al. | |
| 8,197,443 B2 | 6/2012 | Sundar et al. | |
| 8,256,984 B2 | 9/2012 | Fathallah | |
| 8,262,584 B2 | 9/2012 | Eide | |
| D669,096 S | 10/2012 | Katsura | |
| D669,165 S | 10/2012 | Estes | |
| 8,282,565 B2 | 10/2012 | Mahapatra | |
| 8,308,654 B2 | 11/2012 | Eide | |
| 8,398,564 B2 | 3/2013 | Eide | |
| D679,379 S | 4/2013 | Katsura | |
| 8,444,592 B2 | 5/2013 | Williams et al. | |
| 8,480,630 B2 | 7/2013 | Mudd | |
| D687,536 S | 8/2013 | Shafer | |
| 8,545,440 B2 | 10/2013 | Patrick | |
| 8,562,600 B2 | 10/2013 | Kirkpatrick et al. | |
| 8,684,947 B2 | 4/2014 | Eide | |
| 8,764,668 B2 | 7/2014 | Roteliuk et al. | |
| 8,814,807 B2 | 8/2014 | Hulvershorn | |
| 8,896,324 B2 | 11/2014 | Kroh | |
| 8,926,525 B2 | 1/2015 | Hulvershorn | |
| 8,992,481 B2 | 3/2015 | Mudd | |
| 8,998,841 B2 | 4/2015 | Shen | |
| D730,514 S | 5/2015 | Havron | |
| 9,044,542 B2 | 6/2015 | Patrick | |
| D734,475 S | 7/2015 | Ross | |
| D736,370 S | 8/2015 | Bodwell | |
| D741,811 S | 10/2015 | Solomon | |
| 9,199,044 B2 | 12/2015 | Bangera | |
| 9,205,204 B2 | 12/2015 | Bangera | |
| 9,358,038 B2 | 6/2016 | Hulvershorn | |
| 9,358,350 B2 | 6/2016 | Bangera | |
| D760,888 S | 7/2016 | Friedrich | |
| D765,832 S | 9/2016 | Solomon | |
| 9,443,446 B2 | 9/2016 | Rios | |
| 9,452,261 B2 | 9/2016 | Alon | |
| 9,468,396 B2 | 10/2016 | Mahapatra | |
| 9,504,790 B1 | 11/2016 | Hochman | |
| 9,603,537 B2 | 3/2017 | Lechner | |
| 9,642,534 B2 | 5/2017 | Mahapatra | |
| 9,655,528 B2 | 5/2017 | Zhu | |
| D801,519 S | 10/2017 | Sloss | |
| D803,386 S | 11/2017 | Sloss | |
| D803,387 S | 11/2017 | Kerwin | |
| 9,888,881 B2 | 2/2018 | Hulvershorn | |
| 9,901,679 B2 | 2/2018 | Shen | |
| 9,956,341 B2 | 5/2018 | Hockman | |
| 10,004,450 B2 | 6/2018 | Moskowitz | |
| 10,117,673 B2 | 11/2018 | Luo | |
| 10,220,180 B2 | 3/2019 | Hochman | |
| 10,383,610 B2 | 8/2019 | Moskowitz | |
| D859,634 S | 9/2019 | Hochman et al. | |
| 10,406,285 B2 | 9/2019 | Anand | |
| 10,463,838 B2 | 11/2019 | Hulvershorn | |
| 10,602,958 B2 | 3/2020 | Silverstein | |
| 2002/0016567 A1 | 2/2002 | Hochman et al. | |
| 2002/0016569 A1 | 2/2002 | Grotchlow et al. | |
| 2002/0022807 A1 | 2/2002 | Duchon | |

(56) References Cited

U.S. PATENT DOCUMENTS

| | | |
|---|---|---|
| 2002/0143294 A1 | 10/2002 | Duchon |
| 2003/0014006 A1 | 1/2003 | Alexandre |
| 2004/0035743 A1 | 2/2004 | Tighe |
| 2004/0149282 A1 | 8/2004 | Hickle |
| 2004/0215080 A1 | 10/2004 | Lechner |
| 2005/0004513 A1 | 1/2005 | Beyerlein |
| 2005/0004514 A1 | 1/2005 | Hochman |
| 2005/0096593 A1 | 5/2005 | Pope |
| 2006/0122555 A1* | 6/2006 | Hochman ......... A61M 5/16854 604/67 |
| 2006/0247657 A1 | 11/2006 | Trieu |
| 2007/0038143 A1 | 2/2007 | Christensen |
| 2007/0197922 A1 | 8/2007 | Bradley |
| 2008/0058702 A1 | 3/2008 | Arndt |
| 2008/0103408 A1 | 5/2008 | Denton |
| 2008/0281265 A1 | 11/2008 | Hochman |
| 2009/0131832 A1 | 5/2009 | Sacristan Rock et al. |
| 2009/0149911 A1 | 6/2009 | Dacey, Jr. |
| 2009/0149912 A1 | 6/2009 | Dacey, Jr. |
| 2009/0171191 A1 | 7/2009 | Patrick |
| 2009/0210029 A1 | 8/2009 | Tsui |
| 2009/0221914 A1 | 9/2009 | Barrett |
| 2009/0326482 A1 | 12/2009 | Hochman |
| 2010/0022918 A1 | 1/2010 | Fujie |
| 2010/0030102 A1 | 2/2010 | Poston |
| 2010/0049270 A1 | 2/2010 | Pastore |
| 2010/0056932 A1 | 3/2010 | Roteliuk et al. |
| 2010/0179488 A1 | 7/2010 | Spiegel |
| 2010/0274191 A1 | 10/2010 | Ting |
| 2011/0021905 A1 | 1/2011 | Patrick |
| 2011/0046477 A1 | 2/2011 | Hulvershorn |
| 2011/0054353 A1 | 3/2011 | Hulvershorn |
| 2011/0060229 A1 | 3/2011 | Hulvershorn |
| 2011/0087166 A1 | 4/2011 | Davis |
| 2011/0112511 A1 | 5/2011 | Singer |
| 2011/0120566 A1 | 5/2011 | Ohml et al. |
| 2011/0190596 A1 | 8/2011 | Hacker |
| 2011/0270179 A1* | 11/2011 | Ouyang ............. A61B 1/00062 604/110 |
| 2011/0288481 A1 | 11/2011 | Mudd |
| 2011/0298628 A1 | 12/2011 | Vad et al. |
| 2011/0301500 A1 | 12/2011 | Maguire et al. |
| 2012/0022407 A1 | 1/2012 | Lechner |
| 2012/0083760 A1 | 4/2012 | Ledford |
| 2012/0101410 A1 | 4/2012 | Lechner |
| 2012/0232389 A1 | 9/2012 | Guzman |
| 2012/0259237 A1 | 10/2012 | Axelrod |
| 2012/0289819 A1 | 11/2012 | Snow |
| 2012/0296176 A1 | 11/2012 | Herbst |
| 2013/0041258 A1 | 2/2013 | Patrick |
| 2013/0053851 A1 | 2/2013 | Schmitz |
| 2013/0131633 A1 | 5/2013 | Mudd |
| 2013/0261533 A1 | 10/2013 | Norkunas |
| 2014/0012226 A1 | 1/2014 | Hochman |
| 2014/0066891 A1 | 3/2014 | Burns |
| 2014/0121636 A1 | 5/2014 | Boyden |
| 2014/0121637 A1 | 5/2014 | Boyden |
| 2014/0207050 A1 | 7/2014 | Gonzalez |
| 2014/0221965 A1 | 8/2014 | Regittnig |
| 2014/0316268 A1 | 10/2014 | Kafiluddi |
| 2014/0343406 A1 | 11/2014 | Damjanovic |
| 2015/0150519 A1 | 6/2015 | Glenn |
| 2015/0283365 A1 | 10/2015 | Dacey, Jr. |
| 2015/0374929 A1 | 12/2015 | Hyde |
| 2016/0135712 A1 | 5/2016 | Holochwost |
| 2016/0136363 A1 | 5/2016 | McClellan |
| 2016/0228633 A1 | 8/2016 | Welsch |
| 2017/0106142 A1 | 4/2017 | Hochman |
| 2018/0064870 A1 | 3/2018 | Hochman |
| 2018/0087517 A1 | 3/2018 | Glenn |
| 2018/0116551 A1 | 5/2018 | Newman |
| 2018/0228968 A1 | 8/2018 | Hochman |

FOREIGN PATENT DOCUMENTS

| | | |
|---|---|---|
| EP | 0538259 | 4/1993 |
| FR | 2628625 | 9/1989 |
| HU | P8806113 | 10/1990 |
| HU | P0204296 | 3/2003 |
| JP | 5042218 | 2/1993 |
| JP | 6007440 | 1/1994 |
| JP | 6142114 | 5/1994 |
| WO | 1996005768 | 2/1996 |
| WO | 9725081 | 7/1997 |
| WO | 03/000146 | 1/2003 |
| WO | 2010/071416 | 6/2010 |
| WO | 2017066732 | 4/2017 |
| WO | 2018152225 | 8/2018 |
| WO | 2018204668 | 11/2018 |

OTHER PUBLICATIONS

Iff, I., et al., "The use of an acoustic device to identify the epidural space in cattle", The Veterinary Journal 187 (2011) pp. 267-268.

Iff, Isabelle, et al., "The use of an acoustic device to identify the extradural space in standing horses", Veterinary Anaesthesia and Analgesia, 2010, 37, pp. 57-62.

Lechner, T.J.M. et al., "Clinical results with a new acoustic device to identify the epidural space", Anaesthesia, 2002, 57, pp. 768-772.

Lechner, T.J., et al., "Clinical Results with the Acoustic Puncture Assist Device, a New Acoustic Device to Identify the Epidural Space", Anesth Analg. 2003, pp. 1183-1187.

Lechner, T.J.M., et al., "Thoracic epidural puncture guided by an acoustic signal: clinical results", European Journal of Anaesthesiology 2004; 21, pp. 694-699.

Lechner, T.J.M. et al., "The use of a sound-enabled device to measure pressure during insertion of an epidural catheter in women in labour", Anaesthesia, 2011, 66, pp. 568-573.

Tsui, Ban C.H., et al., "Reduced Injection Pressures Using a Compressed Air Injection . . . ", Regional Anesthesia and Pain Medicine, vol. 33, No. 2 Mar.-Apr. 2008: pp. 168-173.

Jonathan Dillon, "Embedded storage in disposable medical items"; Article posted on Aug. 1, 2011; https://www.electronicproducts.com/Digital_ICs/Memory/Embedded_storage_in_disposable_medical_items.aspx.

"Medical Device Sanity"; http://mdgoo.blogspot.com/2014/12/another-medical-device-supplier-with.html; published prior to Oct. 27, 2017.

Maxim Integrated Product Specification for DS28EC20 20Kb 1-Wire EEPROM; published prior to Oct. 27, 2017.

Extended European Search Report issued in European Patent Application No. 13813314.5 dated Feb. 18, 2015.

Examination Report issued in Australian Patent Application No. 2013287174 dated Oct. 26, 2016.

International Search Report issued in International Patent Application No. PCT/US16/63861 dated Mar. 6, 2017.

International Preliminary Report on Patentability issued in International Patent Application No. PCT/US13/45142 dated Jan. 15, 2015.

International Preliminary Report on Patentability for PCT/US2013/045142 Filed on Jun. 11, 2013.

Official Action issued in U.S. Appl. No. 11/208,400 dated May 29, 2008, 10 pages.

Abstract of: Bilbao et al., "Neurological complications associated with ultrasound-guided interscalene and supraclavicular block in elective surgery of the shoulder and arm. Prospective observational study in a university hospital", Rev Esp Anestesiol Reanim, vol. 60, No. 7, Aug.-Sep. 2013, pp. 384-391.

Abstract of: Vas, "A study of epidural pressures in infants", Pediatric Anaesthesia, 11 (5), pp. 575-583, 2001.

Cohen et al., "Functional deficits after intraneural injection during interscalene block", Regional Anesthesia and Pain Medicine, vol. 35, No. 4, Jul.-Aug. 2010, pp. 397-399.

Gadsden et al., "Opening Injection Pressure Consistently Detects Needle-Nerve Contact during Ultrasound-guided Interscalene Brachial Plexus Block" Anesthesiology, vol. 120, No. 5, May 2014, pp. 1246-1253.

(56) References Cited

OTHER PUBLICATIONS

Hadzic et al., "Combination of intraneural injection and high injection pressure leads to fascicular injury and neurologic deficits in dogs", Regional Anesthesia and Pain Medicine, vol. 29 No. 5 Sep.-Oct. 2004, pp. 417-423.
Hirabayashi et al., "Effect of Extradural Compliance and Resistance on Spread of Extradural Analgesia", British Journal of Anaesthesia, 65, pp. 508-513, 1990.
Husemeyer et al., "Lumbar Extradural Injection Pressures N Pregnant Women", British Journal of Anaesthesia, 52, pp. 55-59, 1980.
International Preliminary Report on Patentability issued in International Patent Application No. PCT/US16/57264 dated Apr. 17, 2018.
International Search Report and Written Opinion issued in International Application No. PCT/US16/57264 dated Mar. 22, 2017.
Kapur et al., "Neurologic and histologic outcome after intraneural injections of lidocaine in canine sciatic nerves", ACTA, Anaesthesiologica Scandinavica, vol. 51, 2007, pp. 101-107.
Liu et al., "Incidence of unintentional intraneural injection and postoperative neurological complications with ultrasound-guided interscalene and supraclavicular nerve blocks", Anaesthesia vol. 66, 2011, pp. 168-174.
Lupu et al., "Nerve expansion seen on ultrasound predicts histologic but not functional nerve injury after intraneural injection in pigs", Regional Anesthesia and Pain Medicine, vol. 35, No. 2, Mar.-Apr. 2010, pp. 132-139.
Paul et al., "Extradural Pressure Following the Injection of Two Volumes of Bupivacaine", British Journal of Anaesthesia, 62, pp. 368-372, 1989.
Reiss et al., "Nerve injury complicating ultrasound/electrostimulation-guided supraclavicular brachial plexus block", Regional Anesthesia and Pain Medicine, vol. 35, No. 4, Jul.-Aug. 2010, pp. 400-401.
Sites et al., "Incidence of local anesthetic systemic toxicity and postoperative neurologic symptoms associated with 12,668 ultrasound-guided nerve blocks", Regional Anesthesia and Pain Medicine, vol. 37, No. 5, Sep.-Oct. 2012, pp. 478-482.
Sites et al., "Characterizing novice behavior associated with learning ultrasound-guided peripheral regional anesthesia", Regional Anesthesia and Pain Medicine, vol. 32, No. 2, Mar.-Apr. 2007, pp. 107-115.
Steinfeldt et al., "Forced needle advancement during needle-nerve contact in a porcine model: Histological outcome", Anesthesia & Analgesia, vol. 113, No. 2, Aug. 2011, pp. 417-420.
Steinfeldt et al., "Histological consequences of needle-nerve contact following nerve stimulation in a pig model", Anesthesiology Research and Practice, vol. 2011, Feb. 2011, 9 pages.
Usubiaga et al., "Epidural Pressure and Its Relation to Spread of Anesthetic Solutions in Epidural Space", Anesthesia and Analgesia, vol. 46, No. 4, pp. 440-446, 1967.
Widmer et al., "Incidence and severity of complications due to femoral nerve blocks performed for knee surgery", The Knee, Nov. 2012, 5 pages.
Al-Aamri, et al., "Reliability of Pressure Waveform Analysis to Determine Correct Epidural Needle Placement in Labouring Women", Anaesthesia 2017, 72, pp. 840-844.
Cohen et al, "Epidural Block for Obstetrics: Comparison of Bolus Injection of Local Anesthetic with Gravity Flow Technique", Journal of Clinical Anesthesia, 9, 1997, pp. 623-528.
Cohen et al, "Extradural Block in Obstetric Patients: Review of Experience with Gravity Administration", Acta Anaesthesiologica Scandinavica, 35, 1991, pp. 676-679.
Dawkins, "The identification of the epidural space" Anaesthesia, vol. 18, No. 1, Jan. 1963, pp. 66-77.
McKendry et al., "Pressure Waveforms to Assess Epidural Placement: Is There a Role on Delivery Suite?", Anaesthesia, 72, 2017, pp. 815-820.
Ghia, et al, "Confirmation of Location of Epidural Catheters by Epidural Pressure Waveform and Computed Tomography Cathetergram", Regional Anesthesia and Pain Medicine, vol. 26, No. 4 Jul.-Aug. 2001, pp. 337-341.
Gong et al, "Pressure Waveform-Guided Epidural Catheter Placement in Comparison to the Loss-of-Resistance Conventional Method", Journal of Clinical Anesthesia, 26 (2014) pp. 395-401.
Hong et al, "Analysis of Epidural Waveform for Cervical Epidural Steroid Injections Confirmed with Fluoroscopy", An.md-journal.com, Hong and Jung Medicine (2018) 97:13, 4 pages.
Lennox et al, "A Pulsatile Pressure Waveform Is a Sensitive Marker for Confirming the Location of the Thoracic Epidural Space", Journal of Cardiothoracic and Vascular Anesthesia, vol. 20, No. 5 Oct. 2006, pp. 659-663.
Leurcharusmee et al, "Reliability of Waveform Analysis as an Adjunct to Loss of Resistance for Thoracic Epidural Blocks", Regional Anesthesia and Pain Medicine, vol. 40, No. 6, Nov.-Dec. 2015, pp. 694-697.
Suwa et al, "Pressure-Guided Method for Identification of the Epidural Space in Children", Anesthesiology, vol. 89, No. 2, Aug. 1998, pp. 546-548.
Hsu et al, "The Frequency and Magnitude of Cerebrospinal Fluid Pulsations Influence Intrathecal Drug Distribution: Key Factors for Interpatient Variability", www.anesthesia-analgesia.org, vol. 115, No. 2, Aug. 2012, pp. 386-394.
Wagshul et al, "The pulsating brain: A review of experimental and clinical studies of intracranial pulsatility", http://www.fluidsbarrierscns.com/content/8/1/5, 2011, 8:5, 23 pages.
Hettiarachchi et al, "The Effect of Pulsatile Flow on Intrathecal Drug Delivery in the Spinal Canal", Annals of Biomedical Engineering, vol. 39, No. 10, Oct. 2011, pp. 2592-2602.
Hilber et al, "A systematic review of the diagnostic accuracy of epidural wave form analysis to identify the epidural space in surgical and labor patients", http://www.minervamedica.it, Minerva Anestesiologica, Apr. 2019, 85(4), pp. 393-400.
Iff et al., "The Use of an Acoustic Device to Identify the Extradural Space in Standing Horses", Veterinary Anesthesia and Analgesia, 37 (2010) pp. 57-62.
Hungarian Novelty Report for Application No. P. 04 00176.
NL Search Report, NL 2002708, dated Oct. 9, 2009.
PCT International Prelminary Report on Patentability, PCT/NL2010/000061, dated Oct. 4, 2011.
PCT International Search Report, PCT/NL2010/000061, dated Aug. 23, 2010.
International Search Report and Written Opinion issued in International Application No. PCT/US18/31096 dated Sep. 10, 2018.
Ross et al., "Pressures of Injection in a Cadaver Model of Peripheral Nerve Blockade", Journal of Anesthesia & Clinical Research, 2014, vol. 5, Issue 10, 4 pages.
Product brochure "PAJUNK: NerveGuard Automatic system for injection pressure limitation" (XS200192B) dated Jan. 2017, 4 pages.
https://www.dermaqueen.co.ki7, published prior to Feb. 15, 2017.
http://www.intranixtech.com/myoguide-system/, published prior to Feb. 15, 2017.
http://www.anteis.com/AestheticDermatology/injectionsystem.php, published prior to Feb. 15, 2017.
International Search Report & Written Opinion issued in International Application No. PCT/US13/45142 dated Sep. 10, 2013.
International Preliminary Report on Patentability issued in International Application No. PCT/US06/29091 dated Feb. 28, 2008.
Gadsden, et al., "High Opening Injection Pressure Is Associated With Needle-Nerve and Needle-Fascia Contact During Femoral Nerve Block", Regional Anesthesia and Pain Medicine, vol. 41, No. 1, Jan.-Feb. 2016, pp. 50-55.
Lacoste, "DSSS in a nutshell the Powerof Patterns at Play", Circuit Cellar, Apr. 2020, #357, pp. 62-67.
International Search Report & Written Opinion issued in International Application No. PCT/US20/29857 dated Jul. 21, 2020.

* cited by examiner

DISPOSABLE ASSEMBLY FOR DRUG INFUSION WITH PRESSURE SENSING FOR IDENTIFICATION OF AND INJECTION INTO FLUID-FILLED ANATOMIC SPACES

PRIORITY CLAIM

The present application is a continuation of co-pending U.S. patent application Ser. No. 13/540,880, filed Jul. 3, 2012. The entire disclosure of the foregoing application is incorporated herein by reference.

FIELD AND BACKGROUND OF THE INVENTION

The present invention relates generally to improvements to the delivery of drugs, particularly to systems for subcutaneous injection/aspiration into a fluid filled space of the body. More specifically the invention provides a method and device to identify a fluid-filled tissue space of the body by stopping fluid flow based on a predetermined pressure measurement and resuming fluid flow once the pressure drops below a predetermined pressure measurement.

A regional anesthesia block of epidural tissue-space is understood to produce effective transient anesthesia of the lower extremities of the body. It can be effectively used for a vast number of invasive procedures of the body, including but not limited to child birth, prosthetic hip replacement and a variety of other surgical procedures where anesthesia below the waist is required. It can also be effectively used for treatment of chronic and acute pain including, for example, "back-pain," ailments of the vertebrae and, compression of the accessory nerves of the spinal column. To achieve effective regional anesthesia and to block nerve transmission to the CNS an adequate volume of a local anesthetic solution must be deposited in close proximity to the spinal cord at a particular level of the vertebral column within the anatomic site known as the epidural "space."

The epidural space is that part of the vertebral canal not occupied by the dura mater and its contents. It lies between the dura and the periosteum lining the inside of the vertebral canal. It extends from the foramen magnum to the sacral hiatus. The anterior and posterior nerve roots in their dural covering pass across the epidural space to unite in the intervertebral bodies, and the intravertebral discs. Laterally, the epidural space is bordered by the periosteum of the vertebral pedicles, and the intervertebral foramina. Posteriorly, the bordering structures are the periosteum of the anterior surface of the laminae, the articular processes and their connecting ligaments, the periosteum of the root of the spines, and the interlaminar spaces filled by the ligamentum flavum. The space contains venous plexuses and fatty tissue which is continuous with the fat in the paravertebral space.

The epidural fluid filled space (posterior epidural space) is a limited anatomic area with an irregular shape measuring in several square millimeters with respect to cross section of the vertebrae and spinal column. The fluid filled space is very narrow and is associated closely with the dura of the spinal column with the ligamentum flavum closely adjacent. The fluid filled space therefore has to be clearly identified when the bevel or point of the needle exits the ligamentum flavum, as the dura will be punctured if the needle continues to penetrate. The standard technique for locating the epidural fluid filled space employs the "loss-of-resistance" technique. This technique utilizes a low-friction syringe made of plastic or glass connected to an epidural Tuohy needle (16 to 18 gauge).

The block can be performed with the patient either in the sitting or lateral decubitus position. The patient should be encouraged to adapt a curled-up position, as this tends to open the spaces between the spinous processes and facilitates the identification of the intervertebral spaces. Epidural injections can be sited at any level along the lumbar and thoracic spine, enabling its use in procedures ranging from thoracic surgery to lower limb procedures.

The clinician palpates the vertebral column at the appropriate level of the vertebral column between vertebrae. Local anesthesia is placed within the superficial tissues rendering the tissues of the area to be locally anesthetized. The dermis is then punctured using the Tuohy needle and the needle is advanced while the clinician simultaneously applies pressure on the plunger of the syringe. The pressure on the plunger will unintentionally result in an amount of fluid continuously exiting out of the needle within the tissues.

Insertion of the epidural needle continues and advances through the supraspinous ligament, with the needle pointing in a slightly cephalad direction. The needle is advanced into the interspinous ligament, which is encountered at a depth of 2-3 cm, until the subjective sensation of increased resistance is felt as the needle passes into the ligamentum flavum. The needle is further advanced until the subjective "feel" of resistance by the clinician results in a distinct "back-pressure" on the plunger. The clinician must subjectively differentiate the "back-pressure" or resistance encountered to identify the location of the anatomic structure of the ligamentum flavum. The epidural fluid filled space is entered by the tip of the needle after it passes through the ligamentum flavum.

A known deficiency of this technique is loss of fluid into the tissues when the tip of the needle is in the interspinous ligament as the tissues there are not particularly dense.

The movement of the Tuohy needle from penetration of the dermis to identification of the ligamentum flavum can vary from greatly in depth depending on the patient's physical size. Overweight patients present a greater challenge, and with the morbidly obese patient it may not be a suitable technique because of the limitations of subjective nature of this technique. Age appears to be an additional complicating factor because of the challenge presented by the reduced size of the anatomy of the epidural tissue-space. Small children are often subject to the more dangerous procedure of general anesthesia as a result.

Unfortunately, if the epidural procedure is not performed properly additional fluid is injected within the tissues indiscriminately while trying to determine the location of the fluid-filled epidural space. The additional fluid released into these tissues can further complicate the identification of the fluid-filled space.

Additionally, if the Tuohy needle moves once the epidural space has been located, either by removal of the syringe or inadvertent movement of the patient or doctor's hand, the needle can either be unknowingly moved outside the epidural tissue-space or at worst advanced into dura of the spinal cord producing what is termed a "wet-tap", which can have dangerous long-term consequences to the patient. Even if the epidural space was initially properly located, if the needle further advances during the injection of the anesthetic solution it may deposit a bolus of anesthetic solution into the spinal cord resulting in transient or permanent nerve damage.

Infusion pumps devices and systems are well known in the medical arts, for use in delivery or dispensing a prescribed medication to a patient. Several attempts have been made to adapt these devices for the administration of an epidural injection.

Prior art references are known which attempt to utilize a pressure transducer to measure the pressure within the syringe (see U.S. Pat. No. 5,295,967 to Rondelet et al.). A major deficiency of these systems is their inability to adjust the flow rate and/or pressure of the fluid to compensate for changes in resistance throughout the system.

U.S. Pat. No. 7,922,689 to Lechner discloses a device for locating an anatomic cavity that rely on an alarm (i.e. audible or visual warning signal) requiring the operator to manually modulate the drug delivery system during an injection procedure. This device requires the continuous flow of fluid to identify the epidural tissues similar to the "loss-of-resistance" manual syringe technique. In addition, it relies upon a relative audible change related a pressure drop to identify the epidural tissues. The device requires subjective interpretation of events to which the operator must respond. Furthermore, the device provides continuous injection fluid delivery and attempts to generate a sufficient pressure to do so via an automatic syringe pump device. The device does not, however, provide a means for automatically controlling the injection pressure of fluid delivery or for aspiration of drug delivery during use. Thus, the device of U.S. Pat. No. 7,922,689 maintains injection flow rate despite excess fluid pressure that may result in pain and/or tissue damage.

The concept of using pressure as a metric to perform a safe and effective epidural injection has been well documented in the medical literature. Pressure has been used to identify the epidural space and the importance of pressure within the epidural space has been described by a number of researchers over the years utilizing a variety of experimental set-ups. Usubiaga and co-workers discussed the relationship of pressure and the epidural space while performing an injection into the epidural space and tissues (Anesth. Analg., 46: 440-446, 1967). Husenmeyer and White described the lumbar epidural injection technique and relationship of pressure of during injection in pregnant patients (Br. J. Anaesth., 52: 55-59, 1980). Other investigators, including Paul and Wildsmith (Br. J. Anaesth., 62:368-372, 1989) and Hirabayashi et al. (Br. J. Anaesth., 1990 65:508-513), also evaluated the relationships between pressure and the effects of resistance on the administration of an epidural injection. Lakshmi Vas and co-workers have extended these principles into the area of pediatric medicine (Pediatric. Anesth. 11:575-583, 2001). Lechner and co-workers described a system for manual manipulation epidural injections based on pressure feedback (Anesthesia, 57:768-772, 2002; Anesth. Analg. 96:1183-1187, 2002; Euro. J. Anaestheol. 21:694-699, 2004).

The invention herein described improves the reliability and safety of epidural injection administration by limiting the fluid required to identify the epidural space. It also improves upon prior techniques by providing a predetermined pressure limit and a predetermined resumption of fluid flow below said pressure limit. Additionally, audible and/or visual signal information is provided when the system resumes fluid flow thereby detecting needle entry into the fluid filled space of epidural region.

U.S. Pat. No. 6,200,289 to Hochman et al., co-invented by the inventor of the subject application and incorporated herein by reference, discloses an automatic injection device that includes a drive mechanism that causes a therapeutic fluid to flow from a cartridge supported by a cartridge holder, a tube and a handle with an injection needle. The drive mechanism is connected to an electric motor and a sensor positioned at the motor output that measures the force applied by the motor to the drive mechanism. This force is then used to determine an internal characteristic such as a force or internal pressure generated during the injection process. This characteristic is then used as a control parameter by a microprocessor or controller which generates corresponding commands to the drive mechanism. In a particularly advantageous embodiment, the characteristic is used to calculate an exit pressure at which fluid is ejected by the device through an elongated tube. The electric motor is then operated in such a manner that the exit pressure is maintained at a predetermined level to ensure that a patient does not suffer pain and/or tissue damage.

Published patent application US2011/0120566 to Ohmi et al. is from the non-analogous field of non-biological fluid supply methods for semiconductor manufacturing, chemical industrial and medical industrial facilities. The reference is sited, however, for its teaching of discontinuous switching of fluid flow rate using a pressure type flow rate control device. The probing of anatomic space is not contemplated and the person skilled in the art of designing medial treatment apparatuses and methods would not look to this non-analogous art for guidance.

Published patent application US2011/0301500 to Maguire et al. discloses an automated vessel puncture device using three-dimensional near infrared imaging and a robotically driven needle to providing simultaneous real-time diagnostic assays. It teaches that venipuncture is the process of obtaining a sample of venous blood for purposes of performing various tests. Samples are obtained manually from a vein or organ that is close to the surface of the skin by trained personnel, but there are problems inherent with these processes. This reference uses infrared imaging and a robotically driven needle to address the problem but does not use fluid pressure values to help indication the presence of vein or organ. Although pressure is mentioned, this refers to mechanical pressure resisting the movement of the mechanically driven needle to avert injury to the patient, not to fluid pressure in the needle.

Also, see published U.S. patent application US2006/0122555 to Hochman, incorporated herein by reference, which discloses an in-line fluid pressure sensor between a syringe and tubing connected to a needle for injecting the fluid.

Other patents that disclose the use of a mechanical biasing force (rather than a transducer) to locate and control the flow of a fluid are U.S. Pat. Nos. 8,197,443 and 8,137,312 for detection apparatuses and methods.

Also, see U.S. Pat. No. 8,142,414 for methods of injecting fluids into joints using a handpiece assembly, U.S. Pat. No. 8,079,976 for an articular injection system and published patent application US2006/0122555 for a drug infusion device for neural axial and peripheral nerve tissue identification using exit pressure sensing.

Additional more recent work of Lechner is also disclosed in his patent applications US2012/0101410 for unit, assembly, device and method for testing a sensor means provided in a medical localization device and US2012/0022407 for device for locating a structure inside a body.

A need remains for an apparatus and method that can accurately guide the insertion of a needle into a fluid-filled anatomic space having a lower pressure than its surrounding tissues, such as the epidural space near the spine, the intra-articular space in joints, fluid filled vessels of the body, and which apparatus and method can control both injection of fluid into and aspiration of fluid from the epidural space, and which apparatus and method further address the need for maintaining a sterile field and sterile conditions.

SUMMARY OF THE INVENTION

It is an object of the present invention to provide a method and apparatus or device that enables the practitioner to accurately and reproducibly administer an injection to a patient in a desired fluid-filled tissue location. The device and method limit the amount of pain and tissue damage associated with the injection, the risk of complication from a misplaced injection, and, of critical importance, significantly reduce the amount of injection fluid that is administered to non-target tissues. The device utilizes the inherent differences in tissue density or resistance of fluid-filled tissue space and associated pressures which are significantly lower than surrounding organs, connective tissue or other tissues of the body.

Connective tissues of the body have been shown to produce pressures above 200 mm/Hg when injected with a fluid at a rate of 0.07 mL/sec. Each tissue has its own pressure density characteristics which are represented as measurable pressures that can be elicited within a given tissue type. The density or resistance of the tissue is measured using the pressure of a fluid infused from a computer-controlled drug delivery system capable of detecting pressure resistance during infusion. It has also been demonstrated that fluid-filled spaces such as the epidural tissues, the intra-articular space of joints, or vessels of the body have pressures when measured during injection which are well below 200 mm/Hg. In fact, fluid-filled spaces have been found to have significantly lower pressure resistance to fluid-flow closer to zero mm/Hg when infusing into this fluid-filled tissue sites.

Based on the known understanding of an injection with an intended target site of fluid-filled tissue space one can identify the intended site by using a pressurized fluid injection system that will not allow fluid-flow to occur until the needle enters into a fluid-filled tissue space allowing the pressure to drop below a said predetermined pressure within the tissues. The device, by using a predetermined maximum pressure value which automatically prevents continuous drug flow into surrounding tissues and will only resume drug flow once the pressure drops below a further predetermined value, enables the identification of a fluid-filled space based on the resumption of fluid-flow during an injection.

The device can utilize a single or two different predetermined pressures (e.g. a first and third pressure) to stop fluid flow and another (e.g. second) predetermined pressure to resume fluid flow during an injection. It is also possible that the first predetermined pressure is used to stop fluid-flow and the second predetermined pressure is selected to resume fluid-flow once the identification of a fluid-filled space is achieved. Both will effectively limit the placement of a fluid into unintended tissues by eliminating the need for a continuous flow of fluid during the placement of a needle and allow the identification of a fluid-filled space once the resumption of fluid-flow occurs within patient tissues. It is also possible to include the third predetermined pressure which can stop fluid-flow at a determined pressure limit which is lower than the first predetermined pressure limit described above. This provides an even greater level of safety for the injection of a fluid if the needle should migrate out of the target during an injection to the patient.

Thus, an injection device of this invention includes a fluid reservoir (fluid storage device), an injection fluid, a pumping mechanism, an end in fluid contact with the reservoir and adapted to be inserted into the body of a patient, a sensor arranged to determine a resistance measurement of the injection fluid, and a controller capable of receiving the resistance measurement from the sensor, calculate a pressure, and modulating the flow rate of the injection fluid. The sensor may be an in-line sensor placed between the pumping mechanism and the end, but is preferably between the pumping mechanism or syringe and the beginning of the tubing set which measures the pressure of the injection fluid. Alternatively, the sensor may be within the mechanical arm.

A sensor, such as a transducer, is used to sense the force or pressure generated by the motor and applied by the plunger within the fluid storage device. In one aspect of the invention, the transducer measures the force between the carpule adapter and the remaining housing of the device. In another aspect of the invention, the transducer includes a size sensing device that senses a change in dimension of an element of the device, said change being indicative of the force or pressure of the drug within the system and the pressure. For example, the change in size of the tubing may be used as an indicium of this force or pressure. In another embodiment, the pressure within the tube is measured externally and used as a means of determining the fluid pressure.

It is contemplated that the controller is capable of accepting user-inputted parameters including, for example, a pre-set maximum pressure, a pre-set resumption pressure and a pre-set flow rate. The controller is further capable of modulating the flow rate, including reducing the flow rate to substantially zero. The flow rate may be controlled in a binary manner (i.e., at a pre-set flow rate when the measured pressure is less than the pre-set maximum pressure, and off when the measured fluid pressure is less than the pre-set maximum pressure), or the flow rate may be a function of the pressure (i.e., the flow rate is higher at measured pressures farther below the pre-set maximum pressure). In the latter case, the flow rate may, optionally, be preset to a maximum allowable flow rate. Likewise, the function relating the flow rate to the measured fluid pressure may also be user-defined. In useful embodiments, the pre-set maximum pressure is between about 50 mm/Hg and about 300 mm/Hg, or between about 100 mm/Hg and about 250 mm/Hg.

The pressure resistance measure is optionally converted into a visual as well as audible signal on a continuous basis. The measurements are then presented to the doctor so that the doctor can determine or confirm whether the injection is being delivered to the correct tissues. In addition, the measurements are also recorded for later review and documentation of the clinical event. Upper limits of pressure as well as control of flow-rate can be pre-defined to ensure that excessive pressure and/or flow-rate are not used during this process.

The invention, therefore, provides a method for administering an injection to a patient by providing a fluid reservoir, an injection fluid, a pumping mechanism, and an end adapted for insertion into the patient; pumping the fluid from the reservoir into the patient; calculating the pressure of the fluid at an interface between the end and the tissue of said patient, and controlling the flow rate of the injection fluid such that the pressure does not exceed a pre-set maximum pressure and then the flow rate resumes once the pressure drops below a pre-set pressure.

In one embodiment, the devices and methods of this invention are used to administer an epidural injection. In a second embodiment, the device and method of this invention are used to administer an intra-articular fluid-filled space injection. In both embodiments, the injection fluid contains, for example, an anesthetic and the end is adapted for insertion into the epidural or intra-articular fluid-filled tissue space. It is contemplated that either the pharmaceutical-containing or a pharmaceutical-free (testing) fluid is used to identify the fluid-filled tissue space during the needle placement phase of the procedure. Suitable pharmaceutical-free fluids include, for example, physiological saline, phosphate-buffered saline, artificial cerebral spinal fluid, Ringers, 5% dextrose, or filtered air. Once the fluid-filled tissue space is identified using the pressure difference method, the injection fluid is changed (i.e., requiring a plurality of fluid reservoirs) to a pharmaceutical-containing fluid. The use of a pharmaceutical-free fluid during the needle placement phase minimizes or eliminates the delivery of the pharmaceutical to non-target tissues.

Frequently, procedures that require an epidural injection of anesthetic are lengthy and, in addition to the initial (loading) dose, one or more subsequent (maintenance) doses are required. Typically, an indwelling catheter is used to administer the plurality of doses. In another embodiment, the invention provides a method for administering an epidural injection requiring a plurality of injections wherein, during administration of the second (and subsequent) doses, the pressure of the fluid at an interface between the end and the tissue of said patient is calculated, and the flow rate of the injection fluid during said second injection is controlled such that the pressure does not exceed the pre-set maximum pressure. Likewise, this technique may be used for indwelling catheter maintenance (i.e., to determine whether the catheter remains in a target tissue such as the epidural tissue space) whether or not an additional injection is contemplated or desired at that time.

It is further contemplated that this injection device may be used for aspiration of a fluid-filled tissue space after the identification of a fluid-filled space is determined. Aspiration may be used either to withdraw a sample of tissue or extracellular fluid (i.e., cerebral spinal fluid, intra-articular fluid, blood, etc.), or may be used to determine the correct placement of the injection needle. During an aspiration procedure, the "entry pressure" is measured in the same manner as the pressure within the fluid-filled tissue space, which is characterized by a loss of pressure. Likewise, false loss of pressure is also identified using an aspiration procedure because the internal tissue structure (i.e., cyst) will be quickly drained of its contents and the entry pressure will rise above the threshold entry pressure.

The motor, the coupling associated with the motor and the electronic controller discussed below are at least partially disposed within the apparatus housing for protection.

The fluid storage device is filled and a setup process is initiated during which the clinician places a preloaded syringe into the syringe receptacle on the top of the instrument. The clinician can change the fluid flow rate and peak pressure to be dispensed. Then they operate a touch-screen activation and/or pneumatic control such as a foot pedal and initiate the fluid flow. Alternatively, commands may be initiated by the clinician either electronically or by voice commands. During dispensing, the output from the transducer is used to calculate the current fluid pressure. If this pressure approaches a certain threshold, the fluid flow rate is automatically stopped to prevent excessive injection of drugs into the non-targeted tissues, thereby ensuring that the patient does not suffer undue pain or damaged to tissues from excess fluid-flow. Several optional features are also provided including aspiration, purging or charging the media with or without air.

Throughout the process, the clinician is provided with constant current information on the ongoing process, both visual and aurally, including the current flow rate, total volume ejected or aspired, tissue pressures, entry pressures and other parameters. The slave microprocessor receives commands from the master microprocessor and generates the drive signals required to operate the motor.

In another embodiment, it is possible to have two distinct drives to allow the placement of multiple syringes onto a single device. In such embodiment presented herein, a first drive is used with a separate syringe, tubing set and needle for the delivery of a first drug and a second drive contains a separate syringe, pressure transducer, tubing set and needle for a second drug. Each drive is capable of the features described above. In addition, one of the two drives may also be used without the capacity to sense pressure and be entirely used to delivery a drug at a specific flow-rate. This drive may be used to delivery a local anesthetic prior to the use of the second drive in which a pre-determining pressure limiting feature is used to identify a fluid-filled tissue space.

Since the benefits of limiting drug infusion into the non-targeted connective tissue region of a patient have been described, there is a need at times to provide adequate local anesthetics and other drugs to these tissues without limiting the ability to inject a therapeutic drug such as local anesthetic for the purpose of producing superficial soft-tissue anesthesia prior to attempting to identify a fluid-filled tissue space such as the epidural or intra-articular or other fluid-filled spaces of the body. Hence, an instrument with two drives achieves these objectives.

According to yet another aspect, the present invention provides a disposable fluid flow assembly for operation in connection with a fluid pump configured to provide a flow of fluid to the disposable fluid flow assembly. The fluid pump may comprises a central controller having a memory and the central controller may be configured to control the flow of fluid in response to manual commands input via an input element. The disposable fluid flow assembly includes an elongated flexible tube and a needle hub connected with the flexible tube. The hub is configured for connecting a needle with the hub. The assembly also includes a pressure sensor for sensing fluid pressure that is connected with the tube or the hub. A data line may be provided having a first end electrically connected with the pressure sensor and a second end having an electrical connector for connecting the data line with the fluid pump. Additionally, the assembly includes an identification circuit embedded within or connected to the first electrical connector. The identification circuit is configured to provide a plurality of signals to the central controller of the fluid pump when the disposable needle assembly is connected with the fluid pump. This plurality of signals may include: (i) a configuration signal indicative of the physical characteristics of the disposable needle assembly; (ii) a verification signal indicative of the disposable needle assembly being cooperable with the fluid pump; (iii) a first use signal identifying the particular disposable needle assembly so that the central controller can detect whether the specific disposable needle assembly was previously used.

According to a further aspect, the present invention further provides a disposable fluid flow assembly for operation in connection with a fluid pump configured to provide a flow of fluid to the disposable fluid flow assembly. The fluid pump may include a central controller having a memory and the central controller may be configured to control the flow of fluid in response to manual commands input via an input element. The disposable fluid flow assembly include an elongated flexible tube and a needle hub connected with the flexible tube. The hub is configured to connect a needle with the hub. Additionally, a pressure sensor is provided for sensing fluid pressure. The pressure sensor is connected with the tube or the hub. The assembly may also include a data line having a first end electrically connected with the pressure sensor and a second end having an electrical connector for connecting the data line with the fluid pump. An identification circuit embedded within or connected to the first electrical connector is configured to provide a plurality of signals to the central controller of the fluid pump when the disposable needle assembly is connected with the fluid pump. The plurality of signals include: (i) a configuration signal indicative of the physical characteristics of the disposable needle assembly; (ii) a verification signal indicative of the disposable needle assembly being cooperable with the fluid pump; (iii) a use signal identifying the particular disposable needle assembly so that the central controller can detect the number of cycles or length of time that the disposable needle assembly has been used.

A still further aspect of the present invention provides a disposable fluid flow assembly for operation in connection with a fluid pump configured to provide a flow of fluid to the disposable fluid flow assembly. The fluid pump comprises a central controller having a memory and the central controller is configured to control the flow of fluid in response to manual commands input via an input element. The disposable fluid flow assembly includes an elongated flexible tube and a needle hub connected with the flexible tube. The hub may be configured for connecting a needle with the hub. A pressure sensor for sensing fluid pressure is connected with the tube or the hub. The assembly also include an identification circuit connected with the pressure sensor wherein the identification is configured to provide a plurality of signals to the central controller of the fluid pump when the disposable needle assembly is connected with the fluid pump. The plurality of signals may include: (i) a configuration signal indicative of the physical characteristics of the disposable needle assembly; (ii) a verification signal indicative of the disposable needle assembly being cooperable with the fluid pump; (iii) a first use signal identifying the particular disposable needle assembly so that the central controller can detect whether the specific disposable needle assembly was previously used.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
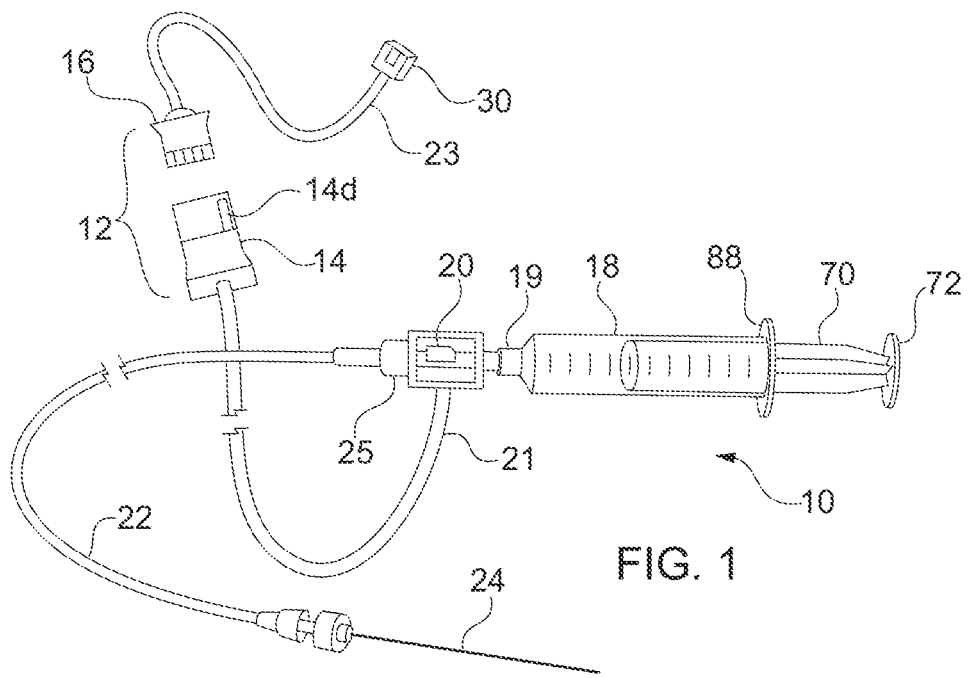
FIG. 1 is a view of an authorized disposables assembly of the invention.
Figure 2:
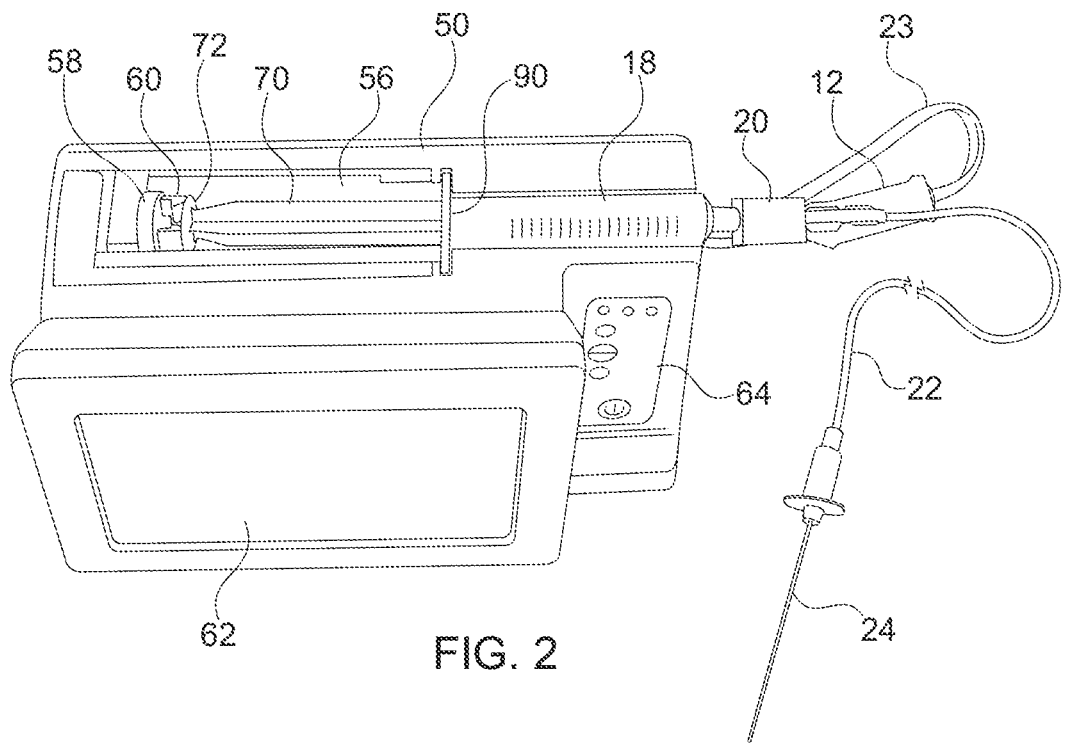
FIG. 2 is a top view of a computer-controlled drug delivery unit housing with a disposables assembly in place for use.
Figure 3:
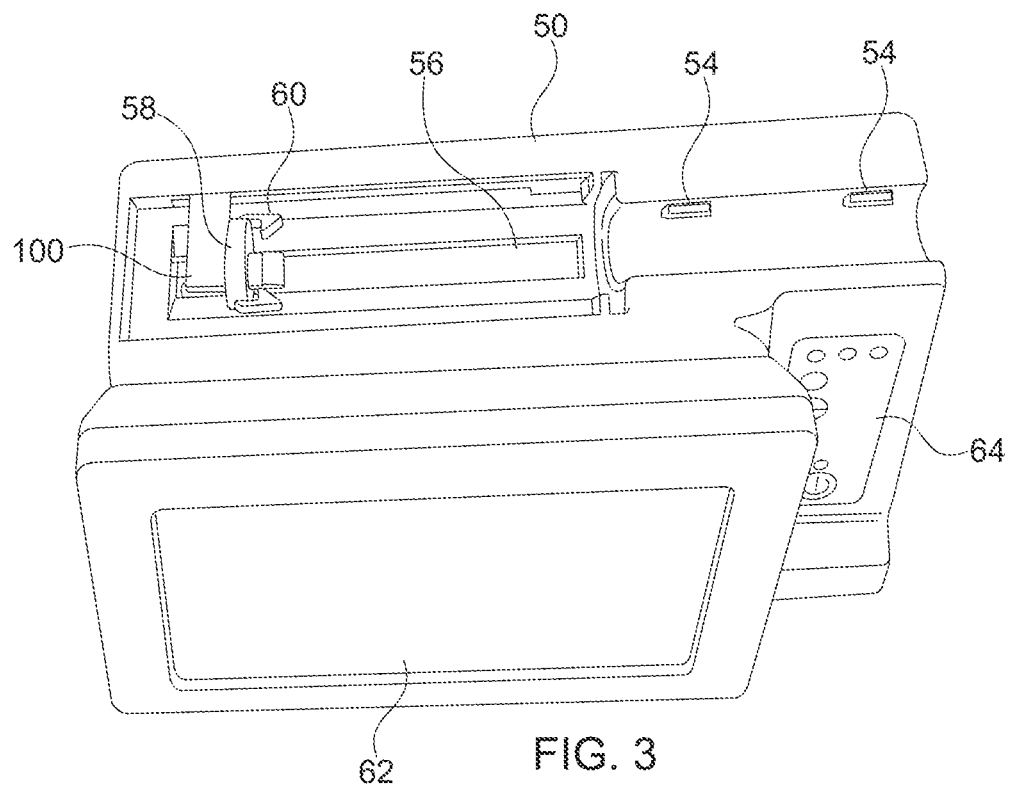
FIG. 3 is a view similar to FIG. 2 of the unit without the disposables assembly.
Figure 4:
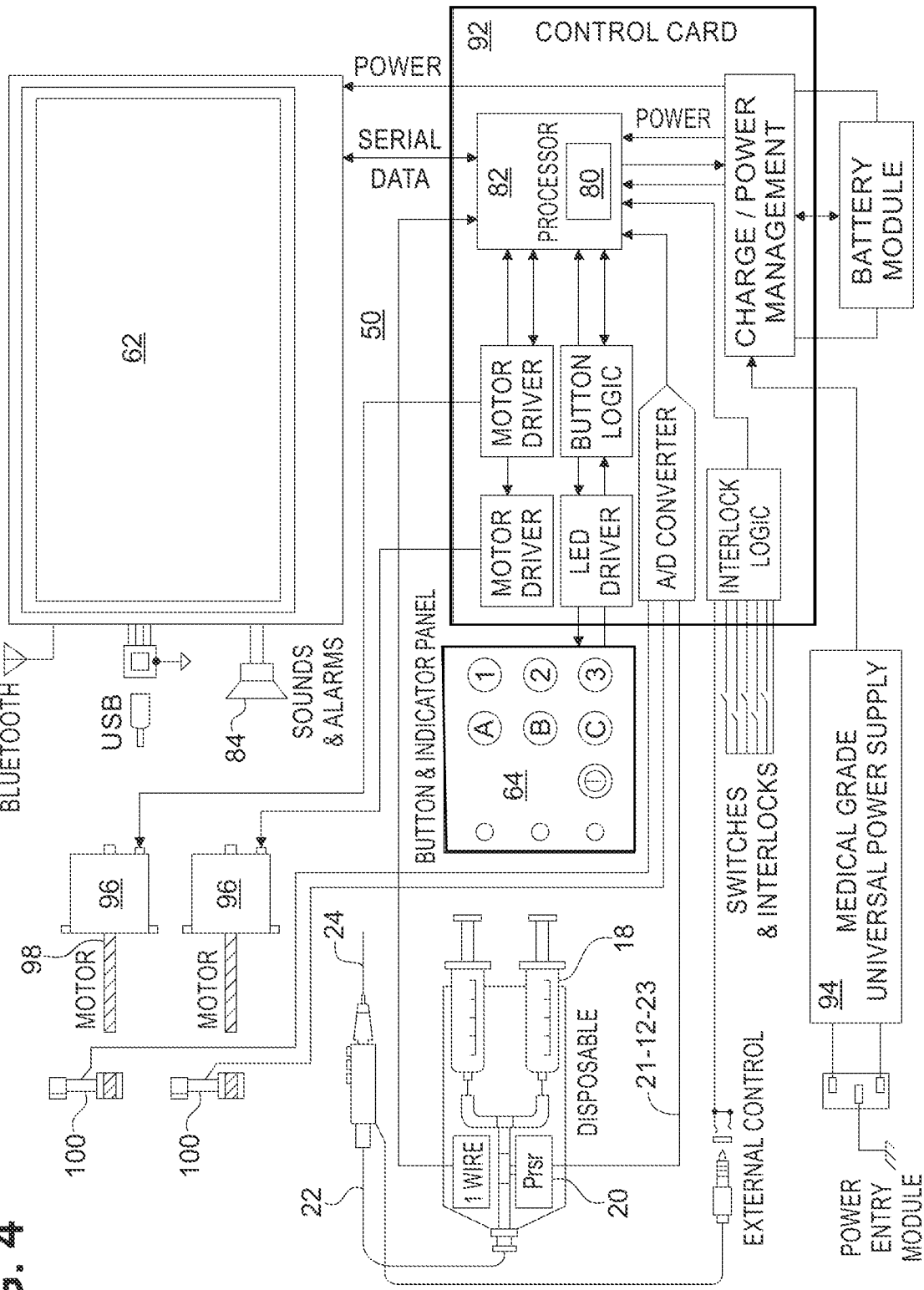
FIG. 4 is a schematic representation of a different embodiment of the computer-controlled drug delivery system of the invention.

Referring now to the drawings, in which like reference numerals are used to refer to the same or similar elements, FIG. 1 shows as disposables assembly 10, made up of various parts that are permanently connected to each other and are supplied in sterile package for single use in conjunction with a computer-controlled drug delivery instrument or drive unit 50 shown in FIGS. 2 and 3, which together form a system schematically shown in FIG. 4.

The subject invention pertains to a system for determining location and delivering drugs in fluid-filled tissues such as the epidural space, intra-articular space, globe of the eye, cysts, vessels and other fluid-filled spaces of the body. The injection of such drugs, such as, but not limited to local anesthetic solutions as, cortico-steroids, hydroxyapatite, joint replenishment drugs, sclerosing agents and other drugs are typically injected into a fluid-filled tissue space for therapeutic purposes. Importantly, due to a variety of factors, injected fluid disperses through a tissue at different rates, causing the fluid pressure to vary. The present inventor has discovered that this pressure (or an internal pressure related to the resistance pressure of a tissue) is indicative of, and may be used to identify several types of tissues.

The present invention provides a method and device that enables the practitioner to accurately identify fluid-filled tissue space while limiting the placement of drugs into non-targeted tissues. This is performed for a diagnostic and therapeutic procedure. The current device utilizes the pressure of a fluid from a needle or catheter ("the injector") following placement of the needle/catheter within the tissue in order to properly identify the accuracy of placement and to monitor the (correct) placement during an injection or aspiration. Specifically, the present device utilizes a pre-determined first pressure to prevent the flow of a drug within a non-targeted (first) tissue site and to resume a flow of fluid once a pressure either drops below a pre-determined same pressure. In an additional embodiment, the device may utilize a first pre-determined first pressure to prevent flow of the drug and a second different pre-determine pressure to which the pressure must enter to allow flow to resume. Utilizing a pre-determined pressure to allow the accurate needle/catheter placement throughout the insertion, injection, and maintenance phases of the procedure. First, the pressure is used during the needle/catheter insertion to identify the anatomical structures and to enable the clinician to correctly determine when the lumen of the injector is placed within the fluid-filled tissue space. Hence, a non-continuous fluid flow of drug is used to identify the intended target tissue.

The pre-determined pressure is also used to prevent flow of the drug at a specified value and then allows fluid-flow to resume once a pre-determined pressure value is below said value. This may be used during the maintenance phase of the procedure to ensure that the injector remains within the intended tissues such as the epidural tissue space. There is a particular risk during medical procedures that require an initial epidural injection (i.e., loading dose) followed by periodic maintenance doses in order to maintain the desired level of anesthesia. Typically, an indwelling catheter is inserted into the epidural space and remains attached to the injection device throughout the procedure. Frequently, the patient is moved between the loading dose and one or more of the maintenance doses. Such movement may cause a correctly placed catheter to migrate from the epidural tissue space into a non-target tissue. The present device monitors the pressure during all periodic doses (i.e., the loading dose and all subsequent maintenance doses). Thus, drug will not be injected into tissues that are unintended and non-therapeutic to the patient. Additionally, the clinician is alerted should the catheter migrate during the maintenance phase. The current device utilizes non-continuous fluid-flow and pre-determined pressures to properly identify the accurate placement of an indwelling catheter while limiting the flow of drug into non-targeted tissues.

Thus, the advantages of the present device over the prior art include (i) a means to identify the fluid filled tissue space such as the epidural, intra-articular, globe of the eye, cysts and blood or other fluid vessels, but not limited to these structures, while utilizing a negligible volume of drug-containing solution, (ii) a means to identify non-targeted tissues by limiting the flow of drug from a first pre-determined pressure limit. (iv) a means to monitor the placement of a needle/catheter for the entire duration of catheterization (i.e., during the maintenance phase of drug infusion) by monitoring the flow of drug into a fluid-filled space.

According to the principles of this disclosure, the pressure is measured using the pressure/force of a fluid injected/infused from a computer-controlled drug delivery system capable of detecting pressure resistance during infusion. The pressure resistance measure is converted into a visual as well as audible signal on a continuous basis while the fluid flow of drug is non-continuous. The computer-controlled drug delivery system is continuously modulated based on the pressure generated producing a non-continuous fluid flow. Thus, the flow-rate is variable and is dependent on the pressure of the system. It is contemplated that the pressure is the primary controlling variable of the system.

The flow-rate, therefore, becomes a secondary variable that is modulated within a pre-determined range in order to maintain the desired fluid-flow. In one specific embodiment, the fluid flow is stopped at pressures exceeding a pre-determined threshold (maximum pressure). The flow-rate, as a secondary variable, may be limited so that fluid injections are not unduly rapid under low pressure conditions. It is contemplated that the relationship between pressure and fluid flow rate may either be binary or continuous. A binary relationship exists when the injection device is configured to deliver a fluid at a single, pre-determined flow rate for any pressure less than the pre-set maximum. Thus, the fluid flow is either on or off based on whether or not the pressure exceeds the threshold. Alternatively, the flow rate may be modulated by as a function of pressure. In this case, flow rate will be reduced as the maximum pressure is approached and increased as the pressure drops. Optionally, the flow rate may be limited to a first pre-set maximum pressure and a flow rate resumes at a second distinct pre-determined pressure.

It is also contemplated that the injection device optionally may contain a means for recording and/or displaying relevant injection data including, for example, instantaneous flow rates, pressures, and injection amounts. All measurements and information may be presented to the clinician in "real-time" so that the clinician may determine whether the injection is being delivered to the intended location and/or correct tissues and may modify the injection technique accordingly. In addition, the measurements may be recorded for later review and documentation of the clinical event.

It is also contemplated that multiple syringes driven by separate syringe plungers may be used to allow multiple drugs to be injected as well as a second syringe drive that does not required a pre-determined pressure to be reached for any said purpose. The second drive can be programmed on a specific flow-rate to allow infusion of a drug such as local anesthetic and other therapeutic drugs into a variety of tissues.

In yet another embodiment the device may contain two distinct syringe drives in which both are capable of modulation based on fluid-pressure as previously herein described.

Authorized Disposables Assembly

The invention includes a new design of a disposables assembly or disposable assembly, made up of syringe, pressure-transducer, tubing set and needle plus one of a variety of unique proprietary connection adaptors (disclosed herein is called an "ID-Connector" or abbreviated as "ID-Connector") to be affixed as part of the disposable assembly used in conjunction with a computer-controlled drug delivery system. FIG. 1 illustrates one embodiment of the disposable assembly of the invention.

The computer-controlled drug delivery system of the invention, illustrated in FIGS. 2, 3 and 4, provides numerous benefits to patients by providing a more accurate injection. The invention also provides numerous clinical benefits for practitioners by producing superior outcomes. Instruments embodying the invention are shown to provide a more precise and safer administration of drugs for a variety of application such as epidurals, interarticular and other subcutaneous injections. Ensuring the use of only authorized disposables components is critical to the proper performance of such instruments. The selection of incorrect components could lead to a number of undesirable outcomes including:

1. Incorrect volumes administered.
2. Improper flow-rate and pressure measurements.
3. Use of non-fitting components leading to error.
4. Use of poorly designed non-authorized substitute components.

To ensure that the appropriate disposable components are used with the computer-controlled drug delivery system of the invention a proprietary connector 12 in FIG. 1 is included. Connector 12 has first and second mating parts 14 and 16 and has the ability to provide a unique connection and/or electrical circuit connection and/or required data information transfer prior to use. Connector 12 acts as a controlling element between the disposables assembly parts 10, made up of syringe 18, pressure-transducer 20, tubing set 22 and needle 24, and the assembly is connected to the computer-controlled drug delivery instrument 50 of FIG. 2, by a jack 30.

Currently there are no structural means to provide verification of the selection of disposable components used with a computer-controlled drug delivery instrument.

The proprietary adaptor connection 12 of the invention ensures that only authorized, correctly configured, correctly sized and sterilized disposables assemblies 10 are used with the instrument. This is accomplished in the following structural implementations.

The connection 12, electronically connects the in-line, electronic pressure transducer 20 to the computer-controlled drug delivery instrument 50, using an external data cable 21 from transducer 20 to the first mating part 14, that is plugged to the second mating part 16, and is connected by a second cable 23 and the jack 30 that is plugged into the instrument 50. The pressure-transducer 20 is connected inline, that is, immediately between the end 19 of the cylinder of syringe 18, and one end 25 of tubing 22, e.g. by Luer connections that have been permanently bonded as explained below, so that the instantaneous, actual fluid pressure in the drug delivery line is being sensed and used by the instrument, which provides a close approximation to the actual, instantaneous fluid pressure at the point or tip of the needle 24, and therefore, at the location in the patient's body where the tip is located.

The electronic pressure-transducer or sensor 20 provides pressure data via the electronic data cable and connector 21-12-23, that is connected directly to the unit 50 to collect such pressure measurements. By incorporating the intervening proprietary connection 12 between the electronic pressure-transducer 20 and the computer-controlled drug delivery instrument 50, a verification and/or authorization checkpoint can be established. The proprietary connection 12 is used to identify and verify the connected components. The disposable components 10 are provided as an authorized single-use, bonded disposable set in which all components are glued together, i.e. the syringe 18 is permanently bonded to the tubing-set 22 with electronic pressure sensor or transducer 20 permanently bonded there between, up to the first mating part 14, all being permanently bonded to each other. This disposables assembly 10 is used and discarded as a unit. It is further connected to the drive unit 50 by the second mating part 16 that can only be connected to the proprietary first mating part 14 to ensure that only authorized disposables assemblies 10 are used and that they are only used once.

The electronic pressure transducer 20 can, for example be any one of various piezoelectric pressure sensors available from Merit Medical Systems, Inc. such as the Meritrans® Pressure Transducer item MER212.

The proprietary connection 12 disclosed herein is called an "ID-Connector." The ID-Connector 12 is composed of two components, one being the ID-Connector-Plug 14 and the Custom-ID-Connector-Receptacle 16. Since the role of "plug" and "receptacle" can be reversed or each can even have both plug and receptacle features, they are also called first and second mating parts 14 and 16 in this disclosure.

Figure 1A:
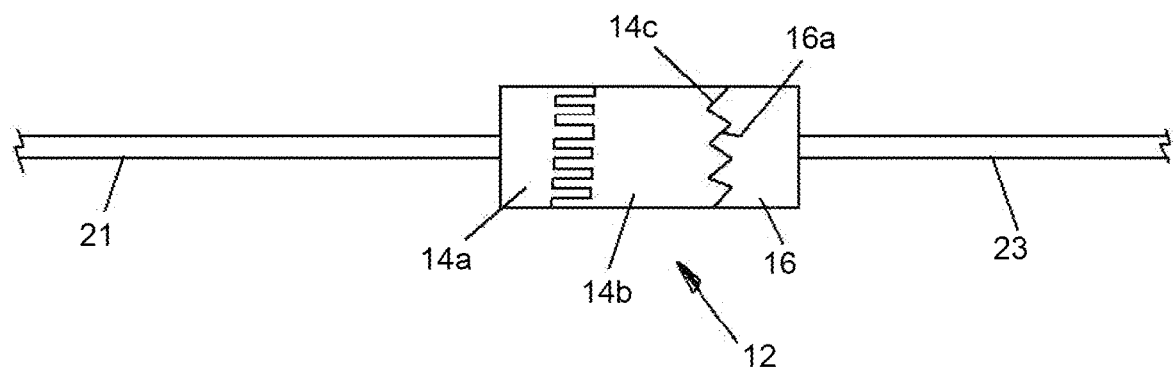
FIG. 1A is a view of one embodiment of a proprietary connector of the invention.

The ID-Connector system 12 is designed as an electronic physical bridge between the instrument 50 and an authorized, bonded-together, disposable set-up or disposables assembly 10. The ID-Connector-Plug 14 has two opposing functional sides 14a and 14b as shown in FIG. 1A, that are plugged into, and permanently bonded with each other. One side 14a is the conventional plug or socket that allows the connection of a standard component such as that from the existing electronic pressure-transducer (i.e. a Meritrans Pressure Transducer item MER212) of disposable components. The opposite side 14b of the ID-Connector 14 is a custom ID-Connector-Plug side and has one end that is conventional and plugs into side 14a, and an opposite proprietary side. As mentioned, sides 14a and 14b are also bonded to each. The Custom-ID-Connector-Plug side 14b connects via its proprietary mating face, i.e., a custom set of projections and depletions 14c, to the second component or the ID-Connector Receptacle 16 via its proprietary mating face, i.e., a complementary set of projections and depletions 16a. This connection of 14c to 16a is detachable so that replacement disposable set-ups 10 can be used. Part 16 is connected to the drive unit 50 via electronic cable 23 and jack 30 as shown in FIGS. 1 and 2. The ID-Connector system or connector 12 is designed in a variety of unique configurations to include additional connection socket/pin combinations as shown in FIG. 1B for a proprietary connection that will provide a unique "signature" to the system, thus providing verification prior to operation.

As illustrated in FIG. 1, another authorization scheme of the invention includes a computer chip, SIM or other uniquely coded circuit 14d that is also electrically connected to the drive unit 50 by the cable 23 when parts 14 and 16 are mated, and which is read by an authorization program or circuit in unit 50. If the coded circuit 14d is genuine, the unit 50 will operate properly, if not, the unit is disabled and a warning such as "Unauthorized Syringe Detected" is posted on the screen of the unit and optionally a warning sound is made, including but not limited to a vocalization of words, an alarm, or other warning signal or any combination thereof. The coded circuit 14d is also coded for a one-use function whereby the authorization program or circuit in unit 50 will detect if a specific disposable set-up 10 was previously used and, if so, again disable the unit 50 and post a warning. The coded circuit 14d can also be coded with the physical (e.g. tubing, needle and syringe gauge) and chemical (e.g. syringe contents) attributes of the disposable assembly 10 that are also read by the circuit or program in unit 50. The coded circuit will then, set, over-ride or modify any settings that are manually programmed into the unit 50, taking into account the attributes of the disposable assembly to insure proper and safe functioning of the unit.

Figure 1B:
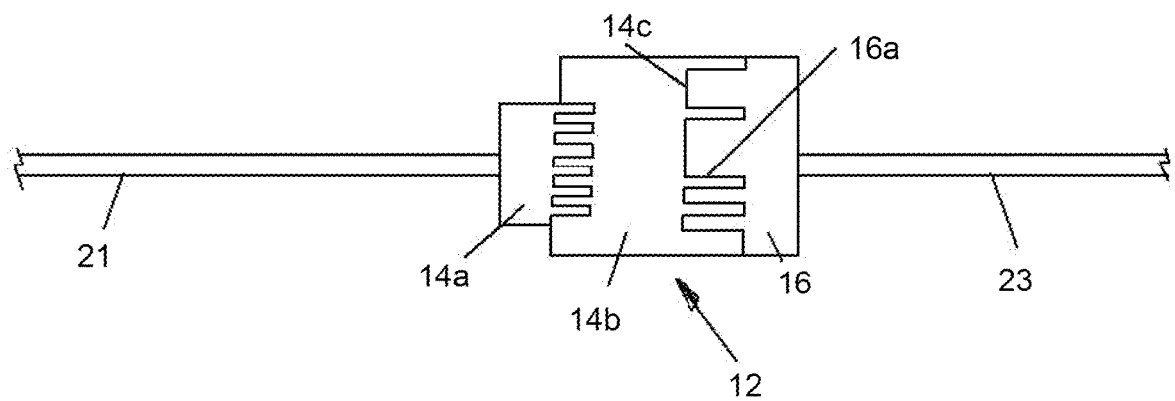
FIG. 1B is a view of second embodiment of the proprietary connector of the invention.

The coding circuit 14d can also be used with or without the mechanical proprietary features of FIGS. 1A and 1B, although using both will increase security. In any case, failure to recognize a proper connection, be it physical, electrical or digital, prevents the operation of the instrument 50.

The invention thus contemplates a new pin connection of the ID-Connector system 12 to complete a required circuit so that the instrument will function to verify, validate and read information from the proper disposables set-up that has been selected for the instrument. The electronic connection in the ID-Connector system provides digital information via stored memory within the circuit 14d of the connector element 12. The new pin connection of the ID-Connector can also provide a unique key/lock interface connection and thereby validating the components to be used in conjunction with the instrument 50.

One or more of any of these above-described security measures can be utilized either solely or in any combination.

The unique ID-Connector system 12 is positioned between the current electronic pressure-transducer 20 and the drive unit 50, but it is anticipated that the ID-Connector system could be bonded, glued or connected to other components to be used with this instrument such as the syringe exclusively or the tubing set exclusively. In the preferred embodiment, the ID-Connector fits between these two connections, however, it is anticipated that this ID-Connector system could be connected at a variety of different interface locations and retain the function intended for verification and identification of the unique disposable set-up.

The attachment 12 performs as follows:
the ID-Connector system is manually attached at the interface junction in a variety of different modalities; and
in a preferred embodiment, the ID-Connector system is part of a complete disposables set-up 10 that comprises syringe, pressure transducer, tubing set and needle.

In the preferred embodiment, the permanent attachment of the needle may be optional so that a practitioner may selection a preferred needle for a particular purpose. The components are assembled individually or as in the preferred embodiment they are glued (i.e. bonded) together and provided as a single disposable set-up ensuring that the proper disposable components were selected.

The preferred embodiment is a bonded-ID-Connector disposable setup. It is anticipated that a variety of configurations could be used in conjunction with the instrument 50. These consist of different size components, i.e. needle, syringe, tubing-set and pressure transducers. The integration of a ID-Connector system ensures the authorized set-up and also possesses the ability to interact with the instrument 50 to confirm and identify the disposable set-up to be used. This represents an important verification to the system. It ensures use of appropriate components and/or drugs. It is anticipated that a pre-filled syringe 18 with a drug could be supplied with the ID-Connector system 12 and disposables set-up 10, or the syringe can be supplied empty so that it can be filled onsite with a desired drug, saline or other fluid. For pre-filled syringes 18, the ID-Connector 12 (in its chip 14*d*) contains the information related to that drug contained within the syringe and presented for use in the instrument.

Improvements over the prior art include an ID-Connector to ensure that the proper selection drug delivery components are utilized with a computer-controlled drug delivery system. The ID-Connector system further resolves multiple deficiencies of a disposable injection system. Importantly, it will not change the workflow practice during the set-up of the instrument while ensuring the use of this novel component. The ID-Connector system does not add additional steps while providing verification of authenticity of components to be used with the overall system and the like. The use of the ID-Connector system also leads to a cost savings when ensuring verification.

Figure 10:
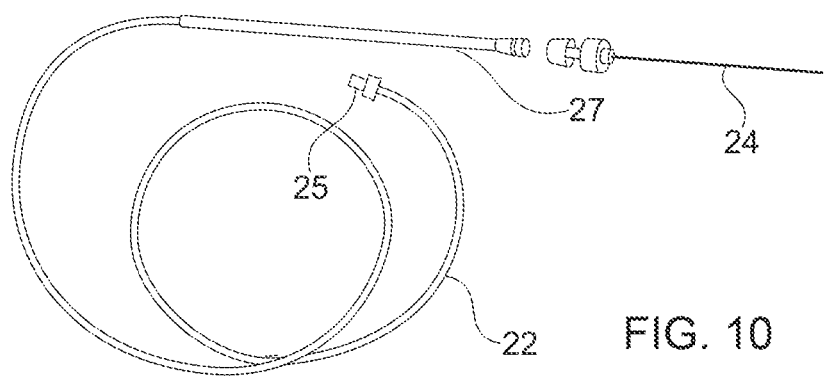
FIG. 10 is a partial exploded view of parts of a disposables assembly with tubing and needle, and further with an elongated handle for connection between the tubing and needle for improving control and dexterity for any type of injection, but in particular useful for improving inferior alveolar injections.

FIG. 10 illustrates parts of a disposables assembly of another embodiment of the invention, namely tubing 22 with end 25 to be permanently fixed to an in-line pressure sensor not shown in FIG. 10. This embodiment includes a rigid, plastic, sterile handle 27 fixed to the opposite end of the tubing 22 and having a male Luer lock that is to be detachably connected to a needle 24 of choice for a particular type of injection into a selected anatomic site. The elongated handle 27 of this embodiment increases manual control and dexterity in placing the needle, in particular because of rotational control. This is particularly important for IA-injections (i.e., inferior alveolar injections), but will enhance epidural and other types of injections as well.

The elongated handle 27 is advantageously about 15 cm long (about 6 inches), or in the preferred range of about 10 to 20 cm long, with tubing 22 of about 122 cm long (about 48 inches).

Pressure-Controlled Injection Device

As described above, the injection device that is exemplified by the drive unit 50 in FIGS. 2, 3 and 4, uses a non-continuous fluid-flow by continuously monitoring a pressure using the electronic pressure-transducer 20, that is preferably the pressure of the fluid during injection. Based on a pre-determined pressure that is set by the practitioner and stored in a memory 80 of a microprocessor or computer 82 of the electronics in unit 50, fluid-flow will stop, and based on a pre-determined pressure fluid-flow, will resume. It is possible that the same pre-determined pressure is used for both of these settings. In such case the pressure will build as fluid initially enters the tissue to a pre-determined level and then stop when the pressure drops below this pre-determined level. Thereafter fluid-flow will resume creating a non-continuous fluid flow.

The invention has defined pre-determined levels of pressure to enable fluid-flow into targeted tissue sites while limiting the flow of drugs into non-targeted tissues. This enables a clinician to selectively inject drugs into specific sites and intended tissues for diagnostic and therapeutic procedures. Preselected maximum allowable pressure limits and/or flow rates are stored in memory 80 and define either the maximum recommended pressures that patients usually tolerate, or other criteria. As the pressure approaches this limit, a visual and/or audible alarm is generated for the clinician, i.e. on screen 62 and via speaker 84 that is activated by data from the microprocessor 82. In addition, data descriptive of the whole injection process is stored for future analysis in memory 80, as discussed above.

Method for Administering Injections into a Fluid-Filled Space

An exemplary method for administering an epidural injection follows. These principles and methods may be easily adapted for injections into tissues and anatomical areas other than the epidural space.

The first pre-determined upper pressure limit is determined by the clinician. Typically, the first pre-determined upper pressure limit is not greater than 200 mm/Hg. It is contemplated that using such a setting the injection system will administer a negligible amount of medication into the connective tissues and a then by selecting a second predetermined pressure below 50 mm/Hg at which the fluid flow will resume. Hence the needle is properly positioned within the fluid-filled space of epidural tissue-space because the pressure within the epidural tissue space is believed to be between about +15 mm/Hg and −15 mm/Hg, whereas the pressure associated with the Ligamentum Flavum is above 200 mm/Hg.

The known pressure measurements within the extra-ligamentary tissues are typically about 100-200 mm/Hg. With the injection device 50 having a second pre-determined pressure at which the fluid flow will resume, that is 50 mm/Hg or below, there will be no significant fluid flow once the needle enters the subcutaneous tissues as the pressure will quickly rise and be maintained as long as the needle resides within the subcutaneous tissues (extra-ligamentary tissues). The clinician, following traditional epidural injection technique, will advance the Tuohy needle and encounter the ligamentum flavum. Still no fluid flow will occur because, as noted above, the ligamentum flavum generates a pressure greater than 100 mm/Hg. Upon penetrating the ligamentum flavum (i.e., needle entry into the epidural fluid-filled space) the pressure will immediate drop below 50 mm/Hg triggering an optional visual display and/or audible tone and/or spoken word such as "Located Epidural," and the drug-containing fluid will begin to flow into the intended target site. Thus, a non-continuous fluid-flow is utilized to identify the targeted tissues. It is possible that the first and second pre-determined pressure values are set to the same number to allow fluid flow to occur only after the pressure drops below a pre-determined pressure.

The pressure sensor 20 or plural sensors of the injection device 50 provide an automatic safety feature in the event that the injection needle leaves the epidural tissue space (e.g., from clinician error or patient movement) or its patency is compromised. If the needle 24 leaves the epidural tissue-space, either by withdrawing through the ligamentum flavum or by contacting the dura, the pressure will immediately rise to a first selected pressure P1, causing a slowing and eventual stoppage of fluid flow at fluid pressures >200 mm/Hg. This has been shown to occur within approximately 2 seconds time (see, Ghelber—Regional Anesthesia and Pain Medicine Vol 33 No 4 2008, page 349 FIG. 2). Optionally, this change in pressure from <50 mm/Hg to >200 mm/Hg will again trigger a visual and/or audible alarm to alert the clinician of improper needle placement. Flow will again automatically resume once the needle is reestablished in the epidural tissue space and the instantaneous pressure at the needle point drops below P1, or, in a further embodiment of the invention, when the pressure drops to a second selection pressure P2 of equal to or below 50 mm/Hg. This automatic safety feature of the injection device helps prevent injection of the anesthetic solution into the spinal cord.

Figure 9:
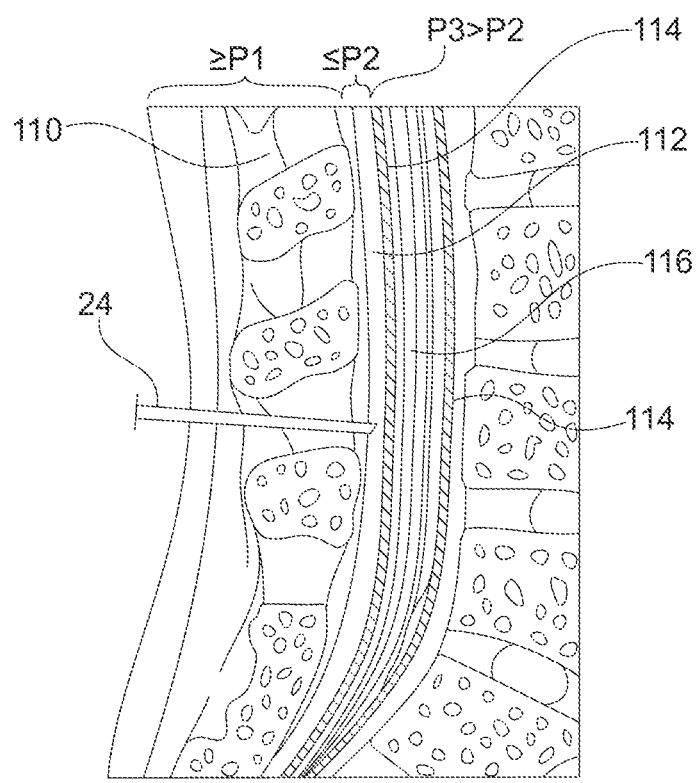
FIG. 9 is a schematic, sectional view through the area of the spine of a subject for an epidural injection, showing the tissues through which a needle will travel, correlated to pressure setting according to the invention.

Turning to FIG. 9, the area of the spine of a subject for an epidural injection is shown. Starting from the outside injection site for the point of the needle 24 at the left in FIG. 9, the tissues in this area include various layers of skin, fat and connective tissue 110, followed by the epidural space 112, that is the anatomic space of interest in a preferred embodiment of the invention. Beyond the epidural space 112 is the dura mater 114 of the spinal cord 116. Clearly it is important that the right-ward progress of the point of the needle 24 through the tissues, stop before reaching the spinal cord and this achieved by the invention. Cross sections of the bones of the backbone in this area are also shown.

According to the invention the microprocessor 82 and memory 80 are programmed with the first pressure P1, of, for example, about 200 mm/Hg, that is selected to be equal to or greater than the instantaneous fluid pressure at the point of the needle as it enters and moves through the tissue 110. At or above this pressure P1, the motor 96 is stopped and the fluid flow to the needle point stops. When the needle point enters the epidural space 112, the instantaneous fluid pressure drops to below P1 and the microprocessor causes the motor to start again to resume fluid flow, now into the epidural space 112 according to one embodiment of the invention. According to a second embodiment of the invention, the second selected pressure P2 stored in memory 80 must be reached before fluid flow resumes. In a third embodiment of the invention, when a third selected pressure P3 stored in memory 80, that is greater than P2 but less than P1, is reached, the fluid flow will stop again. Reaching this third pressure P3 indicates that the needle point has pressed into the dura 114 or is otherwise leaving the anatomic target space. The spaces or layers through which the needle point will travel are correlated to the pressure settings P1, P2 and P3 according to the invention, in FIG. 9.

The first selected pressure P1 for stopping fluid flow is preferable about 200 mm/Hg for an epidural injection, but can be in the range of about 25 to about 300 mm/Hg depending on the tissue to be first punctured by the needle point. Pressure P2 for resuming fluid flow is preferably about 50 mm/Hg for an epidural injection, but can be in the range of about 20 to about 150 mm/Hg depending on the anatomic space of interest. The third selected pressure P3 for stopping fluid flow again, is preferable about 125 mm/Hg for an epidural injection but can be in the range of about 80 to about 180 mm/Hg depending the anatomic space of interest. The use of three set pressure improves the flow/no-flow control as the needle point moves through different tissue types for any fluid-filled anatomic space capable of receiving fluid at a lower pressure than tissues surrounding the anatomic space.

A feature of the present injection device and accompanying method is the ability to quickly and accurately identify a "false-loss-of-resistance" or "false-positive" (typically within 2-4 seconds). A false-loss-of-resistance typically occurs when a traditional loss-of-resistance manual syringe technique is used and a drop of resistance occurs when the epidural needle enters a cyst or less dense space outside the epidural tissue-space. The ligaments in the area are understood to be less dense and a false loss of resistance is not uncommon. Many times, the subjective nature of this anatomic location can lead the clinician to believe he has located the epidural tissue-space. When using the computer-controlled drug delivery system with pressure control, once the needle enters such a space it quickly fills the space or pressurizes the less dense tissue with fluid and the recorded pressure rises above 200 mm/Hg and objectively indicates a "false-loss-of-resistance." This would typically not be the situation using a traditional manual syringe technique or a system that has a continuous fluid flow of drug from a syringe pump. In such cases once the initial loss-of-resistance is encountered, the syringe is moved and the operator delivers the bolus of the fluid (no longer subjectively testing for a "loss-of-resistance") thereby depositing anesthetic solution in an anatomic location outside the intended epidural tissue-space (again see, Ghelber—Regional Anesthesia and Pain Medicine Vol 33 No 4 2008, page 350, FIG. 3 is a line graph demonstrating a false-loss-of-resistance at time of about 250 sec.). This observation is most likely associated with ligamentous tissue, measured during the administration of an epidural injection. The incorrect tissue structure was quickly pressurized, returning the measured fluid pressure >200 mm/Hg. Insertion of the catheter into the epidural space and subsequent fluid injection does not result in a significant and rapid rise in pressure, indicating that the catheter is correctly located.

It is contemplated that a pharmaceutical-free fluid is used to identify the epidural tissue space during the needle placement phase of the epidural procedure. Suitable pharmaceutical-free fluids include, for example, sterile saline, artificial cerebral spinal fluid, Ringers, 5% dextrose, or filtered air. Once the epidural tissue space is identified using the pressure differential, the injection fluid is changed to a pharmaceutical-containing fluid. The use of a pharmaceutical-free fluid during the needle placement phase minimizes or eliminates the delivery of the pharmaceutical to non-target tissues.

Another feature of the current device and methodology is the objective nature of pressure measured by a computer-controlled drug delivery device that is monitored during all phases of the injection process. The clinician, therefore, no longer relies on the subjective nature of a "feel" but rather is provided with objective information of absolute values while performing each phase of this critical technique. Each phase of the technique is improved by the ability to continuously monitor the pressure while using a non-continuous fluid-flow of drug allowing adjustments to be made that ensure greater safety and efficacy of the injection.

In another example, the clinician may reset the pre-determined maximum allowable pressure once the fluid-filled space is penetrated and the injection has begun. As noted above, prior to needle entry into the epidural space, the fluid pressure is greater than 200 mm/Hg so little or no fluid is being delivered. Upon entry of the fluid-filled space the pressure drops below zero and gradually rises to about 1-10 mm/Hg. This drop in pressure initiates the flow of fluid from the injection device. At this time, the maximum pre-set pressure value may be changed to a new, lower, maximum. For example, the pre-determined maximum pressure in which fluid flow stops may be reduced to 25 mm/Hg which will provide an extra level of patient safety in the event that the injection needle contacts the dura mater or is withdrawn from the epidural space. The new pre-determined lower maximum pressure will cause the fluid flow to be arrested sooner, and at lower ectopic injection amounts, than the original pre-set value. The change in pre-determined maximum pressure stop of fluid flow may be performed manually by the clinician or automatically by a control element in the injection device.

It should be understood that the example of 200 mm/Hg as the pre-determined maximum pre-set pressure for stoppage of fluid flow is an example and that either a lower or higher pre-set pressure may be selected at the discretion of the clinician. Also, the second pre-determined 50 mm/Hg pressure value at which fluid flow resumes is an example and that either a lower or higher pre-set pressure may be selected at the discretion of the clinician and is merely illustrative. The principles and techniques may be modified for an injection into almost any anatomical location. What is of particular importance in this embodiment of the method and device is the ability to define and select pre-determined values of pressure to produce a non-continuous flow of drug for diagnostic and therapeutic administration.

The techniques described herein are equally applicable to human and animal tissues.

Non-Continuous Fluid-Flow with One or More Distinct Pressure Limits Combined with an Auto-Detect-Fluid Aspiration In preparation for using the unit 50, and with reference to FIGS. 1, 2 and 3, a disposables assembly 10 of FIG. 1 is removed from its sterile packaging and the pre-filled body of syringe 18 is pressed into a semi-cylindrical syringe cradle 52 defined in the upper surface of the housing of unit 50 as shown in FIGS. 2 and 3. The syringe body 18 is held firmly in place in cradle 52 by a pair of spring-loaded clamps 54 and is kept from moving axially in the cradle 52 by having its finger flange 90, that extends for the top end of syringe 18, engaged within a correspondingly shaped finger flange recess 55. The plunger 70 of syringe 18, that is in its fully extended, syringe-full location shown in FIG. 2, is received in a plunger recess 56 in the upper surface of the unit housing, and is sized amply long, wide and deep to contain and suspend the plunger 70 without contacting it so the plunger can be pressed into the syringe body without obstruction.

A movable stage 58 with three spring-loaded thumb flange catches or hooks 60 that are pivotally mounted to the stage 58, is movable under computer control along the plunger recess 56. As will be explained more fully below, the stage 58 is moved to the right in FIGS. 2 and 3, until the stage 58 is close enough to a thumb flange 72 of syringe 18, to allow facing beveled surfaces of the three hooks 60 to engage the thumb flange 72 form the bottom and its opposite sides, to spread under the continued movement of stage 58, and then snap closed below the thumb flange 72. A sensor in unit 50 then senses resistance to the further movement of stage 58, and the stage stops. Since, at this point, the plunger 70 is effectively axially fixed to the stage 58 by the engagement of the catches 60 on thumb flange 72, any further rightward to leftward movement of the stage 58 will also move the plunger 70 to the right, i.e. to expel fluid form the syringe body, or to the left to aspirate fluid back to the syringe body.

The pressure sensor 20 of the assembly 10 is plugged to the proprietary connector 12 and connector 12 is plugged to the unit 50 via jack 30.

As mentioned, the invention relates to a tissue site location and infusion system utilizing a non-continuous fluid flow with one or more (or—"more then one") pressure limits and auto-detect-aspiration system.

The system is composed of the drive unit 50 and the disposable set-up components 10. The drive unit 50 houses the microprocessor or CPU 82, electronic circuitry board 92, a power supply 94 and electronic motor or motors 96 (since in the embodiment of FIG. 4, two syringes can be accommodated). Each electronic motor 96 rotates a spiral shaft 98 that moves a syringe armature 100 in a forward and reverse direction. The syringe armature 100 contains a load cell sensor to detect force. Armature 100 is connected to the stage 58 to move the stage in either direction. As also mentioned, the disposable set-up 10 comprises the new Identification-Connection component 12, syringe 18, in-line pressure transducer 20, tubing set 22 and needle 24.

Detailed Description of Operational Sequence

Figure 5A:
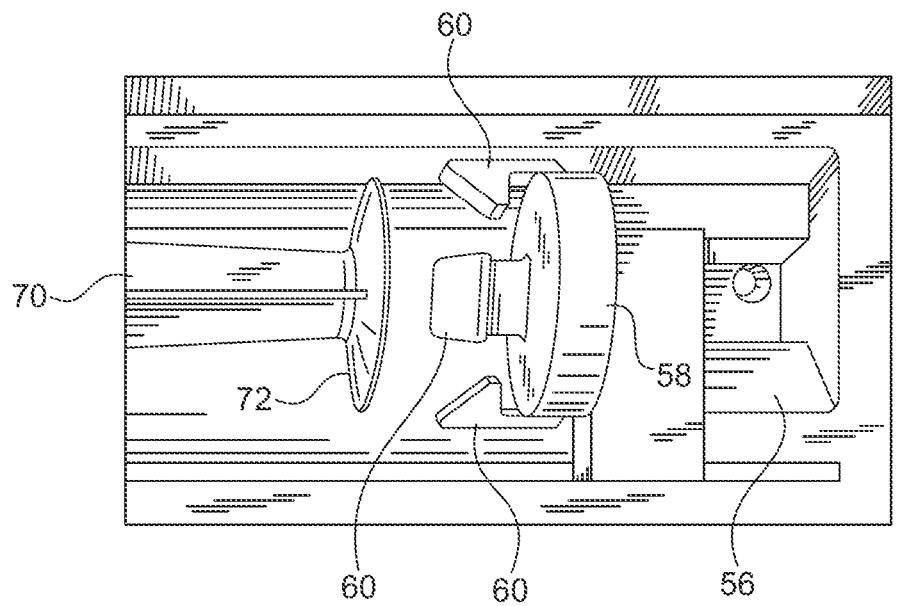
FIG. 5A is an enlarge view of the plunger stage and top end of a syringe plunger of the invention.

The top view of the instrument shows the recessed cavity 52 and recess 56, together called the syringe cradle, which allows the proper positioning to receive a standard 20 cc syringe 18. Contained within the plunger recess 56 is the movable armature 100 and stage 58 that engages the thumb pad or flange 72 of the disposable syringe 18. The mechanism that engages the thumb pad of the syringe has the series of spring loaded hook 60 shown enlarged in FIG. 5A, which automatically capture the syringe thumb pad.

Figure 5B:
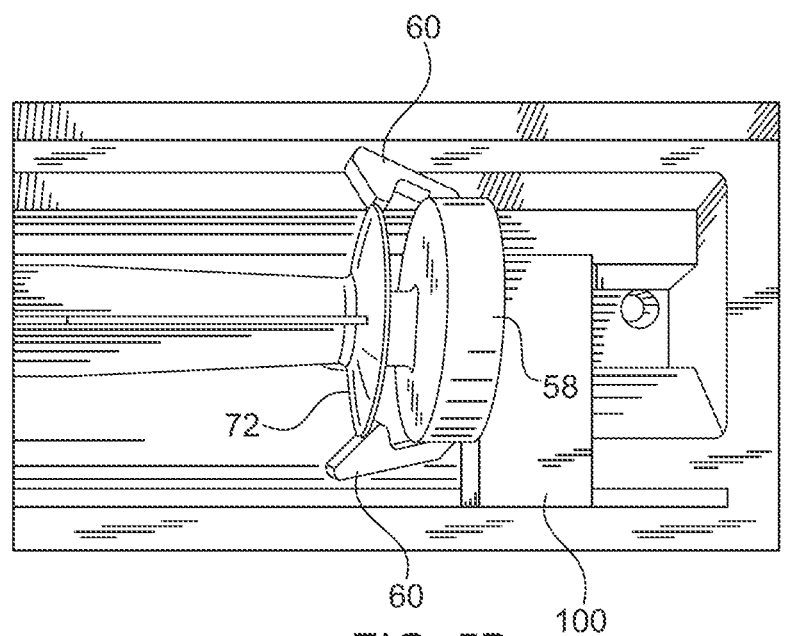
FIG. 5B is an enlarge view similar to FIG. 5A of the stage approaching a thumb pad or thumb flange of the syringe.
Figure 5C:
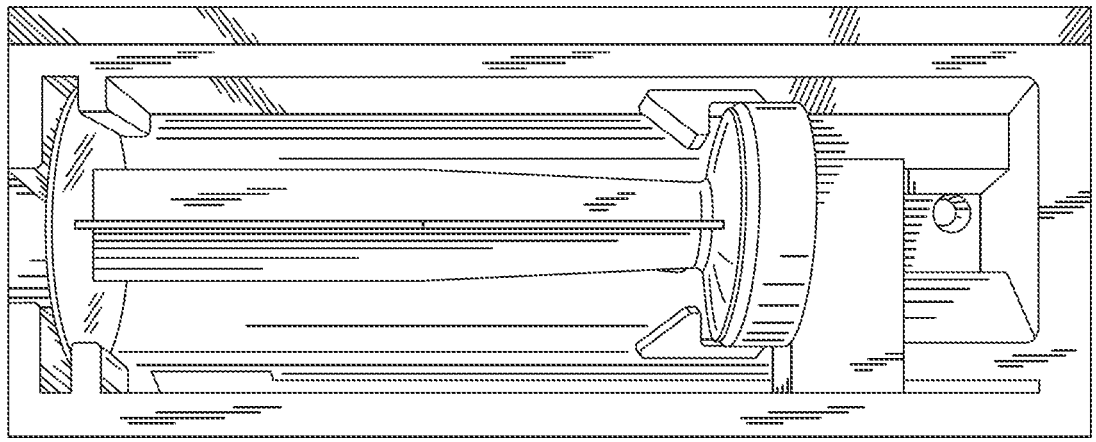
FIG. 5C is an enlarge view similar to FIG. 5A of hooks or catches of the stage engage to the thumb pad of the syringe.
Figure 5D:
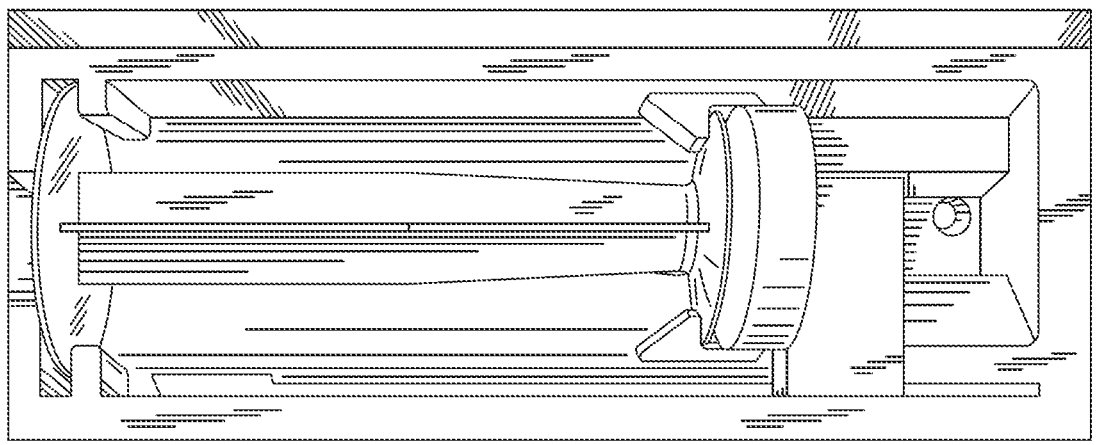
FIG. 5D is an enlarge view similar to FIG. 5A of the stage reversing direction and showing the hooks pull back on the thump pad.

As shown in FIG. 5B, as the thumb pad 72 is engaged, the spring-loaded hooks 60 will move outward, over and then engage the thumb pad in hook-like fashion. This action will secure the thumb pad as shown in FIG. 5C, allowing the syringe stage 58 to mechanically move the syringe plunger 70 in either direction (reverse being shown in FIG. 5D), thus ensuring that aspiration can be performed. Additionally, a force sensor is integrated into the design of the syringe armature 100. The syringe armature 100 uses optical and mechanical features to identify the position of the syringe and can calculate the volume of fluid present within the syringe.

Figure 6:
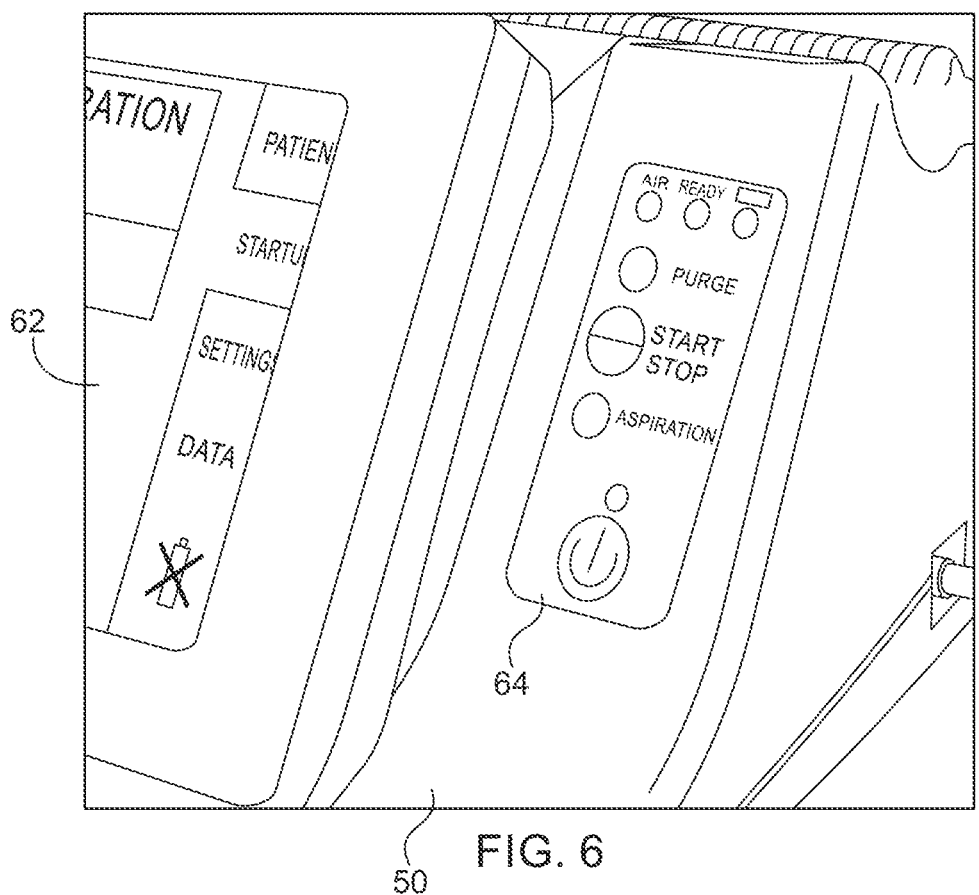
FIG. 6 is a partial view of the drive unit and its side-panel.

Step 1: The drive unit 50 is turned "On" via a separate side-panel 64 shown best in FIG. 6 that includes "On/Off", "Start/Stop", "Purge", and "Aspiration On/Off" buttons and Battery Indictors. The "On/Off" button powers up the drive unit and touch screen interface LCD 62. Turning on power automatically moves the syringe armature mechanism 100 to be in a "home" position shown in FIG. 3.

In FIG. 3 the syringe armature 100 with moving syringe stage 58 with the auto-engage-aspiration thumb-pad receptacle 52, 56 is connected to the movable syringe armature, located on the top of the drive unit.

The top of the drive unit shows feature design, i.e. a syringe cradle, that is designed with detents or clamps 54 on the surface. These detents 54 engage the surface of the barrel of the syringe 18 with an interface as the syringe is placed within the syringe cradle to cause a temporary locking of the syringe into the syringe cradle.

Step 2: The drive unit 50 requires the use of a series of disposable components. As mentioned the disposable set-up 10 of FIG. 1 comprises of the following system components.

A syringe 18—the preferred embodiment uses a standard 20 cc syringe from Becton Dickinson, Inc. The design is not limited to a particular size or volume syringe. The operator will load the syringe with fluid from an appropriate sterile container, such as a multi-dose drug vial or single-use glass ampule. The operator may fully load the syringe or partially load the syringe as the auto-detection feature determines the volume of drug that is contained within the syringe.

The preferred embodiment uses the in-line pressure transducer 20—such as the Meritrans® in-line pressure transducer from Merit Medical, South Jordan, Utah. It is anticipated that the force sensor in the syringe armature could provide information as to fluid pressure and negate the need for a secondary pressure sensor.

A subcutaneous hollow-bore needle 24—in the preferred embodiment a Touhy needle such as the Becton Dickinson 20G×3.5" Touhy Needle. Becton Dickinson, Franklin Lakes, N.J.

Sterile tubing set 22—48" arterial pressure tubing, such as ICU Medical, Inc. San Clemente, Calif.

Identification-Disposable Connector (ID-Connector) 12—the ID-Connector is a proprietary component and part of the invention herein described. It verifies that an appropriate syringe, tubing set, in-line pressure sensor and needle as recommended by the manufacturer of the invention are connected to the drive unit. In the preferred embodiment, the ID-Connect is permanently affixed to the pressure sensor and tubing-set and provided as a single component. It is also possible that the invention includes all disposable elements provided in a distinct kit, allowing the operator to connect the ID-Connector to the individual components for use.

Figure 7:
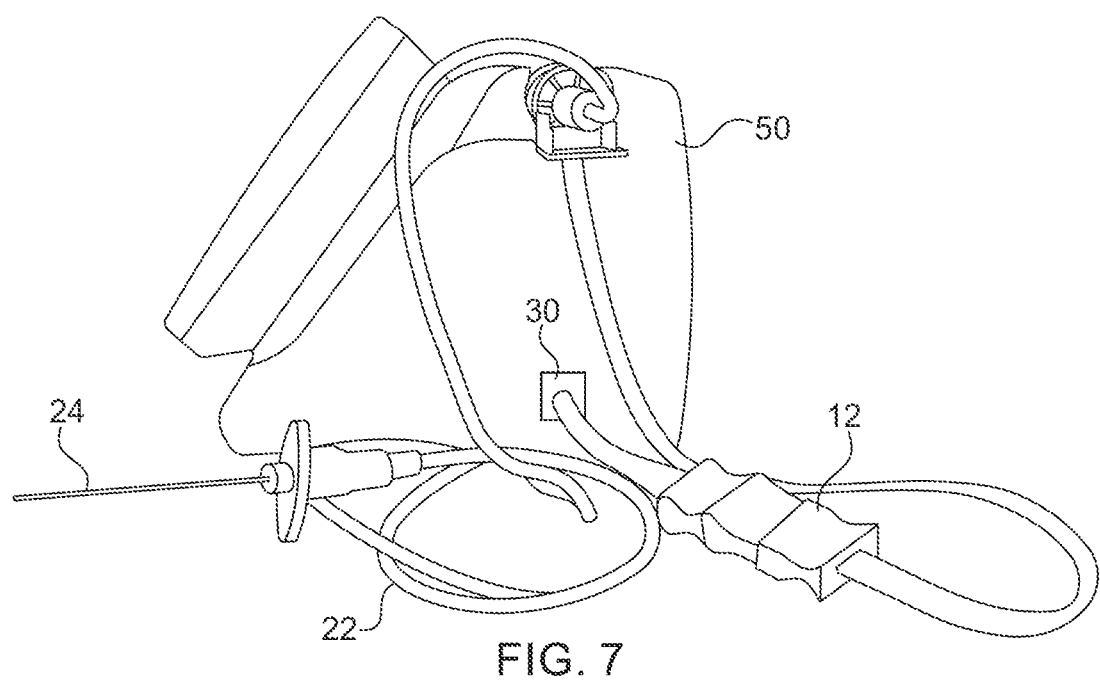
FIG. 7 shown the disposable components connected assembled and the ID-Connector inserted into the side of the drive unit transferring information to/from a CPU in the drive unit.

The ID-Connector is then connected to the drive unit via a removable connection plug 30, such as the RJ-11 plug shown in FIG. 1 and FIG. 7. It is anticipated that an electrical connection other then the RJ-11 plug can be used. A custom electronic plug may be fabricated.

It is anticipated that the ID-Connector may use any and all other means of relying and communicating to the CPU of the Drive Unit including but not limited to InfraRed, WiFi, Blue Tooth or other wireless means.

It is anticipated that the verification of the disposable assembly could also be accomplished using labeling to include bar-coding and a bar-code reader or some other optical means of detection.

The ID-Connector communicates to the CPU of the drive unit to provide information related to the disposable. In the preferred embodiment, the ID-Connector limits the number of cycles the drive unit can operate with the disposable set. This may limit usage based on physical cycling of the drive-unit and/or by measured time. Additionally, it prevents re-use of previously used or non-sterile disposables providing patient safety. The ID-Connector also ensures the proper selection of the disposable components. In the preferred embodiment, the ID-Connector is rigidly connected to as many disposable components as possible, i.e. by glue, heat or chemical bonding to the in-line pressure sensor and tubing set. This is, however, not necessary for the unit to function properly.

It is anticipated that additional information may be encrypted into the ID-Connector such as, but not limited to:
    Drug information such as Drug Name and Formulation, Drug Manufacturer, Lot Number;
    Information related to the disposables assembles;
    Information related to expiration of dates for drug;
    Information related to sterility of disposable kit; and
    Date and time the ID-Connector was used.

In the preferred embodiment, a 20 cc syringe 18 is connected to the Meritrans pressure transducer 20 with attached ID-Connector and 48" Arterial Pressure Tubing set 22. At the distal end of the tubing set a Touhy (hollow-bore) needle 24 is connected such in the FIGS. 1, 2 and 7.

Figure 8A:
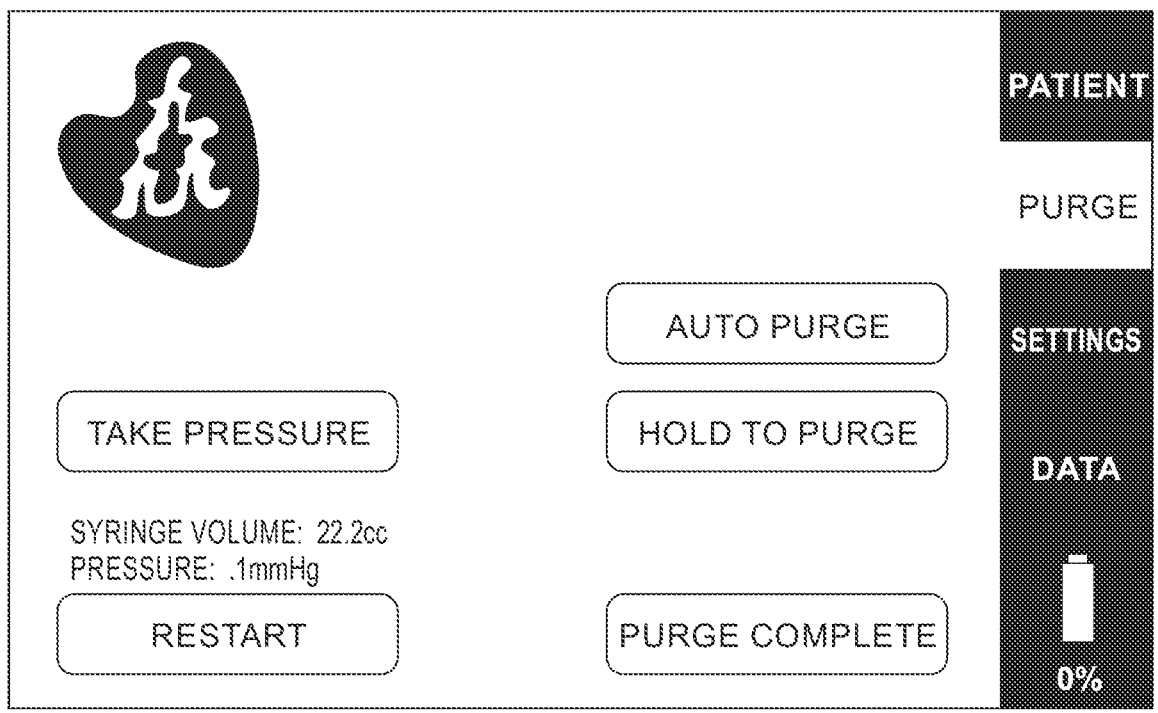
FIGS. 8A to 8G are different screen shots of the touch screen of the drive unit during various phases of operation of the invention.
Figure 8B:

Step 3: After she syringe 18 is inserted in the Syringe-Receptacle, the operator will view an initial screen 62 on the Drive Unit 50 stating "Load Syringe and Press Continue". Touch screen interface 62 allows the operator to touch the "Continue" button which enables the Auto-Engage-Aspiration-Receptacle to make contact with the syringe thumb-pad. See FIG. 8B. The Drive-Unit can detect and confirm that the proper disposables have been inserted into the instrument through a series of features. The confirming design features include:

1. A unique Identification Detector-Connector (ID-Connector)—that is able to communicate with the CPU confirming that the proper disposable assembly has been selected and attached to the Drive-Unit. If the ID-Connector detects an improper selection of disposable assembly or an attempt to Re-Use a disposable assembly, the Drive-Unit will prevent further operation and display a warning message and/or make a signal. The ID-Connector also can limit the number of cycles performed with a given disposable set-up. The ID-Connector controls the system and functions directly and/or indirectly through the CPU. Information is passed to/from the connector in both directions and therefore the CPU can store or alter the content and information on the ID-Connector during operation.

2. The Auto-Syringe-Detection feature utilizes retention hooks of the Auto-Engaging-Aspiration-Receptacle to verify that the proper size syringe is selected. Confirmation is established by the size of the syringe thumb pad and the diameter between the hooks of the Auto-Engaging-Aspiration-Receptacle. If the syringe size and receptacle size are mismatched the hooks cannot engage. The loaded syringe is first detected through a load cell contained drive unit syringe-armature. Forward motion of the syringe-armature is automatically stopped once resistance is detected on the syringe thumb-pad. The syringe-armature will then reverse direction after the spring-activated hooks engage the syringe thumb-pad. In the preferred embodiment, when a smaller diameter thumb-pad is used for a syringe size other than a 20 cc syringe the engaging hooks will not engage and a syringe will not be detected. A warning message is displayed or signal made and further use of the drive-unit is prevented. It is anticipated that different dedicated syringe sizes could be incorporated into specific designs, for example a 10 cc syringe or 5 cc syringe.

The Auto-Syringe-Detection feature also determines the volume of fluid within a syringe by an optical and or mechanical sensor. The volume is displayed.

Once detection of the syringe is completed and confirmed the system can automatically purge an appropriate amount of fluid into the tubing set to fully charge the disposable.

3. In the preferred embodiment the Auto-Purge feature is activated after the Auto-Syringe-Detection feature. This ensures that the proper syringe is installed in the syringe receptacle. It is possible to change a global setting so that Auto-Purge does not occur, in which case a manual-purge option can be used from contacting the touch-screen. It may also be possible to by-pass purging altogether. By-passing "Auto-Purge" and "Manual Purge" is an option when a syringe disposable set up is used multiple times on the same patient, in which case the tubing set would have already been charged from the first purge cycle performed. See FIG. 8A.

Figure 8C:
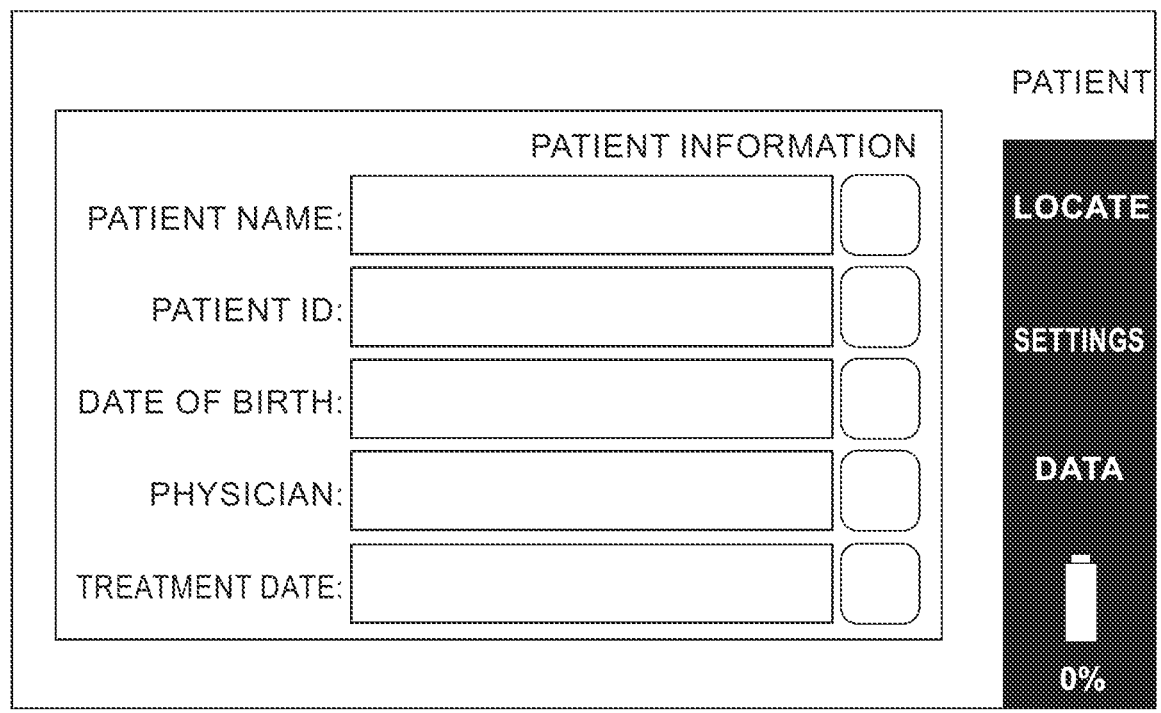

On the far right of the touch screen shown in FIG. 8C is a series of touch-tab's that can be assessed at any time during operation.

1—"Patient" screen: Allows patient/doctor information to be input.
2—"Locate" screen: Active injection screen that shows a visual display of Flow Rate and of fluid pressure during the injection process thereby enabling the operator to locate the target. P1 and P2 values are noted on the screen as well.
3—"Settings" screen: Allows the flow rate and pressure values, P1 value and P2 pressure value to be changed. Screen brightness, Audio-Sound Volume to be selected. Additional features include "Calibrate Touch" touch screen sensitivity and Set Date and Time, Auto-Purge On/Off.
4—"Data" screen: Allows review, electronic transfer and printing of data collected during previous Locate Injection performed.

Patient screen is accessed by touching the "Patient" tab on the right of the screen. Note that the operator can switch between any screen during operation by simply touching the "tab" on the right of the screen.

Figure 8D:
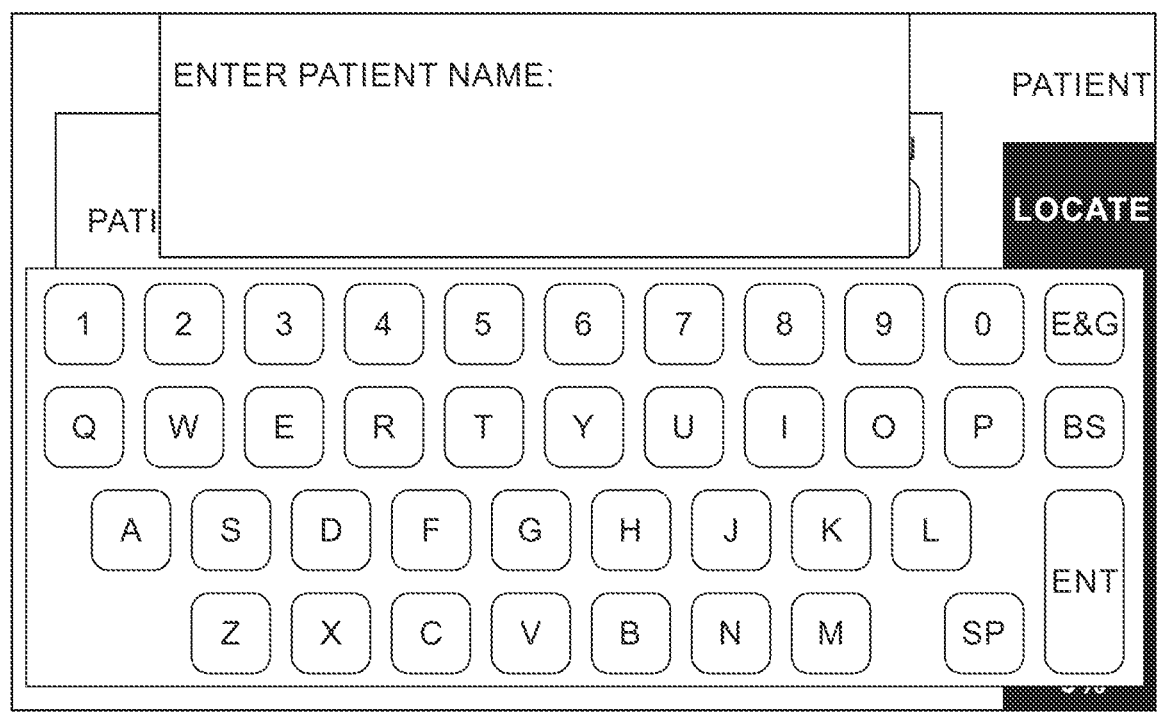

Touching the "Patient" tab displays a screen (namely FIG. 8C) while the operator can input patient and doctor data that will be recorded with a time and date for the patient. See FIG. 8C and FIG. 8D.

Figure 8E:
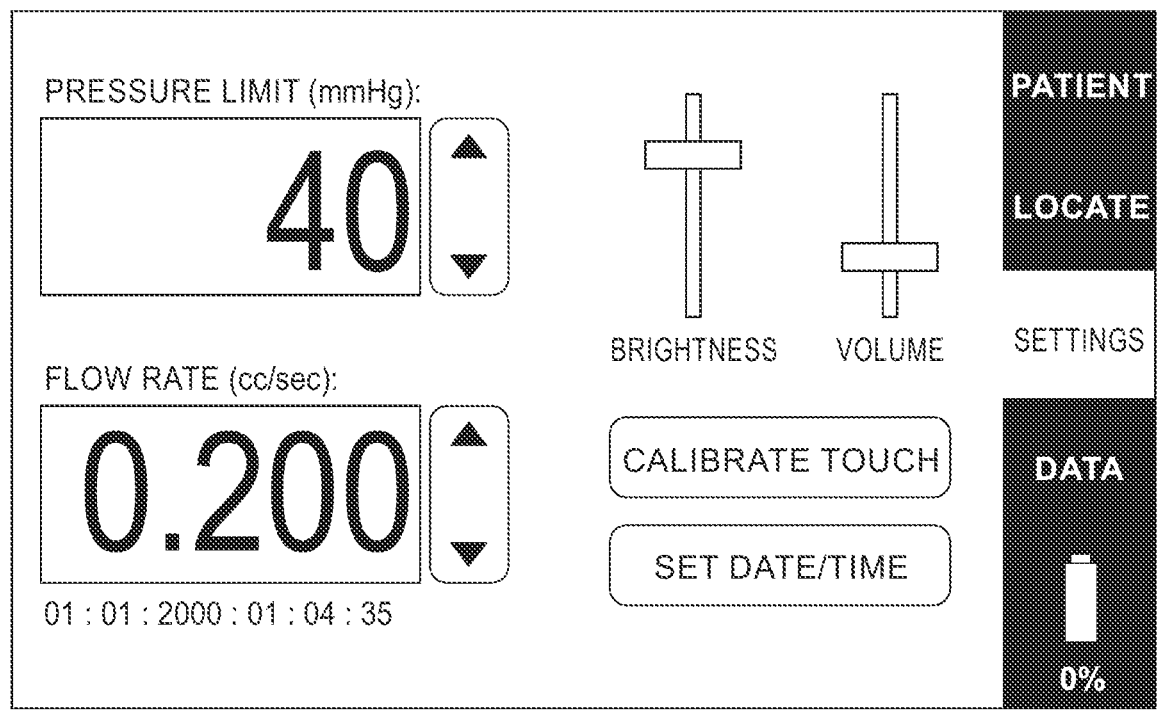

Referring to FIG. 8E, a setting screen displays the following user adjustable settings:

1. "Brightness" to allow the screen to be made brighter or darker. Once selected the screen will default to that value in the future.
2. Audio-Volume adjustment to adjust the sound level during operation.
3. Calibrate Touch to adjust the sensitivity of the touch screen to accommodate for operators using barriers and/or gloves.
4. Set Date and Time to adjust the date and time.
5. Flow-Rate value to adjust the rate selected.
6. Pressure Limit—P1-value. The P1-value is the pressure at which the flow-rate will stop but continues to record, display and announce real-time pressure sensing.
7. Pressure Limit—Start—P2-value. The P2-value is the pressure at which the flow-rate will resume once reached.

In the preferred embodiment, the P1-value and P2-value will be different. The P2-value should be lower then the P2-value, this enables a pressure (P1-value) at which the flow-rate will stop after the pressure attains that initial limit. The flow-rate resume once the pressure identifies a second lower pressure defined as P2-value.

However, it is conceivable that the P2-value could also be higher then the P1-value, in which case the flow rate will only resume when the pressure increases to a new pressure limit. The operator may select the same P1-value and P2-value.

Figure 8F:
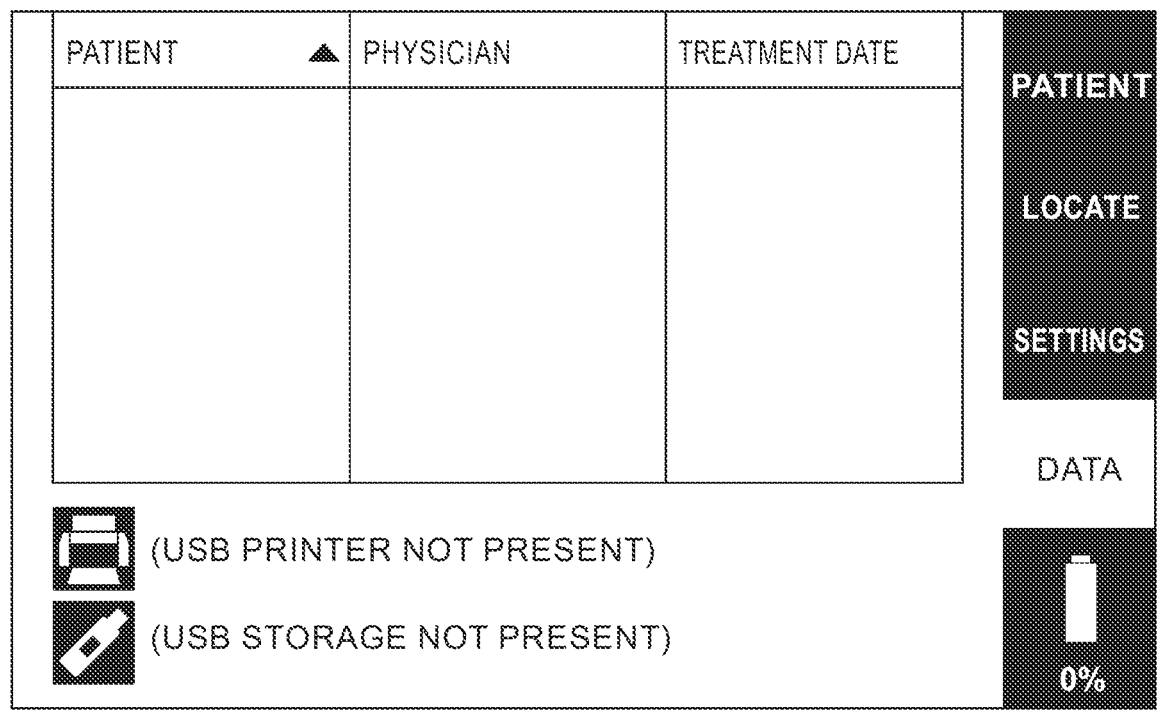

FIG. 8F illustrates data screen that displays patient information and physician information and retains a record of the location and injection event. This information can be stored on a removable medium and/or directly printed to a printer from the drive unit.

Figure 8G:
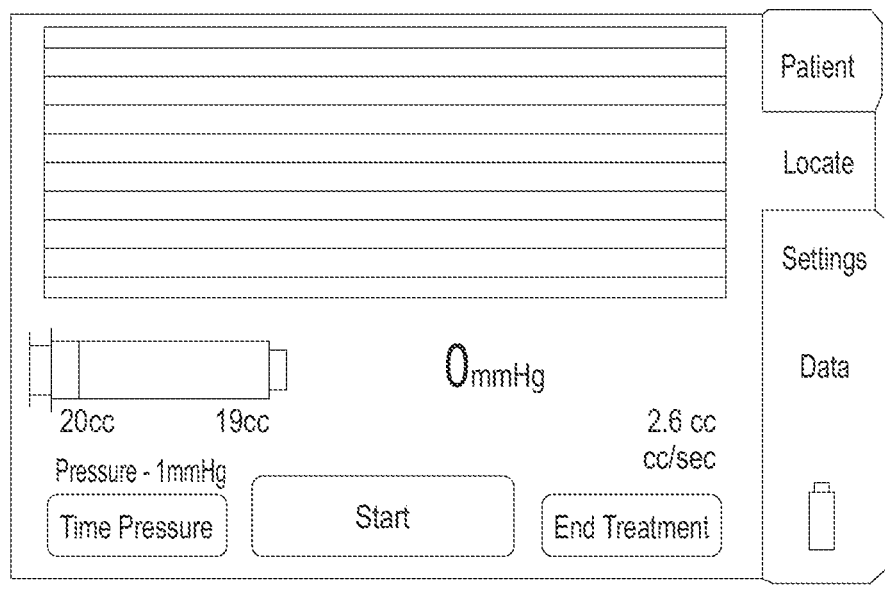

The locate screen provides essential information during the location and injection process of the procedure and is shown in FIG. 8G.

This is the "Locate" mode active screen is viewed during operation. The following touch-screen features can be accessed directly from this screen:

1. "Start"/"Stop" button to start the flow and stop the flow of fluid manual.
2. "Tare Pressure" feature: Allows the system to subtract erroneous pressure reading do to altitude or height discrepancies between the patient and the instrument.
3. "End Treatment" will return the user to the Purge Window to reload either a new syringe set up for a new patient or allow a second syringe to be used on the same patient.
4. "Volume Remaining" is viewed as a graphic image of a syringe. As the fluid is expressed the graphic picture changes to reflect the change in volume showing in the visual.
5. "Pressure" is provided in mm/Hg in real-time during operation.
6. Flow-rate volume that is being used.
7. Visual Graph displaying the pressure reading in a graph format.
8. Audible Sound reflecting the Pressure and Flow of the fluid.
9. P1, and P2 if used, and P3 is used, are represented on the graph of the screen. P2 is noted as a lower pressure limited represented as a highlighted colored horizontal line on the graph itself.
10. "Print"—the operator can print the data and supporting graph from this screen.
11. Time and Date are displayed on the screen.
12. Scrolling Graph—representing the majority of the screen shows a visual representation of the Flow-Rate and Pressure data being recorded. This same information is provided to the user in an Audible tone or signal so that the operator does not have to necessarily view the screen at all times.

Clinical Rational for a Non-Continuous Fluid-Flow with More than One Distinct Pressure Limit Value It is important to set a distinct first upper pressure limit, defined as the first selected pressure P1, that is to stop fluid flow. This limits the quantity of fluid to be injected during the process of identification of the fluid filled tissue space. This is an improvement over the prior art since it prevents continuous flow of fluid into tissues which may have many adverse consequences.

A continuous fluid system was used for the detection of a anatomic fluid filled space, such as the Epidural Space or Intra-Articular Joint Space, in the patents to Timo Lechner (U.S. Pat. No. 7,922,689) and Tim Patrick (U.S. Pat. No. 8,002,736). For these instruments the operator is required to place fluid into tissues on a continuous basis to identify the tissues via pressure. The deficiency of these patents is that a continuous flow of fluid is required during the continuous pressure sensing and identification of an anatomic site or structure. The continuous fluid flow can: 1) cause tissue damage by over-pressurization of tissues; 2) Increase the pressure in the tissue introducing a biasing factor and error to pressure measurements within the tissues leading to failure of intended action; 3) Cause unnecessary intra-operative and post-operative pain; 4) Excessive use of drugs and fluids within the tissue can result in an adverse drug interactions for patients. Therefore, a system that utilizing a non-continuous fluid flow system capable of real-time pressure feedback is distinctly different current inventions represented in the prior art.

Having the ability to set more than one specific pressure value distinctly different from P1 provides a means to detect a Low Pressure Target within an anatomic location without introducing additional fluid. This uses fluid-flow as the detection parameter to identify of a specific anatomic location of the body. It creates a location device that uses a fluid-pressurized system with non-continuous fluid flow based on more than one pressure value limit. This is distinctly different from the CompuFlo technology previously presented in U.S. Pat. No. 7,449,008 Hochman.

While the invention has been described with reference to several particular embodiments, it is to be understood that these embodiments are merely illustrative of the principles of the invention. Accordingly, the embodiments described in particular should be considered as exemplary, not limiting, with respect to the following claims.

What is claimed is:

1. A disposable fluid flow assembly for operation in connection with a fluid pump configured to provide a flow of fluid to the disposable fluid flow assembly, wherein the fluid pump comprises a central controller having a memory and the central controller is configured to control the flow of fluid in response to manual commands input via an input element, wherein the disposable fluid flow assembly comprises:
    an elongated flexible tube;
    a needle hub connected with the flexible tube, wherein the hub is configured for connecting a needle with the hub;
    a pressure sensor for sensing fluid pressure, wherein the pressure sensor is connected with the tube or the hub;
    a data line having a first end electrically connected with the pressure sensor and a second end having an electrical connector for connecting the data line with the fluid pump;
    an identification circuit embedded within or connected to the first electrical connector, wherein the identification circuit is configured to provide a plurality of signals to the central controller of the fluid pump when the disposable needle assembly is connected with the fluid pump, wherein the plurality of signals, including:
    a configuration signal indicative of the physical characteristics of the disposable needle assembly;
    a verification signal indicative of the disposable needle assembly being cooperable with the fluid pump;
    a first use signal identifying the particular disposable needle assembly so that the central controller can detect whether the specific disposable needle assembly was previously used.

2. The disposable assembly of claim 1 comprising an elongated handle, wherein the hub forms a portion of the elongated handle.

3. The disposable assembly of claim 2 wherein the handle is substantially rigid.

4. The disposable assembly of claim 2 wherein the handle has a length and a width and the length is substantially longer than the width.

5. The disposable assembly of claim 2 wherein the flexible tube is substantially longer than the elongated handle.

6. The disposable assembly of claim 1 wherein the identification circuit comprises memory for storing data that uniquely identifies the disposable assembly.

7. The disposable assembly of claim 6 wherein the first use signal comprises the data that uniquely identifies the disposable assembly.

8. The disposable assembly of claim 1 wherein the identification circuit is configured such that the first use signal provides an indication of previous use such that when the first use signal is communicated with the central controller the central controller will prevent operation of the pump if the disposable assembly was previously used.

9. The disposable assembly of claim 1 wherein the fluid flow assembly comprises a pre-filled syringe comprising fluid and the configuration signal comprises data regarding the fluid in the syringe.

10. The disposable assembly of claim 1 wherein the identification circuit provides a control element between the pressure sensor and the central controller when the disposable assembly is connected to the fluid pump.

11. The disposable assembly of claim 1 wherein the identification circuit is configured to ensure that only correctly sized and sterilized disposable assemblies are connected with the fluid pump.

12. The disposable assembly of claim 1 wherein the configuration signal comprises data regarding the length and diameter of the elongated tube.

13. The disposable assembly of claim 1 wherein the identification circuit is configured so that the signals provided by the identification signal override settings stored in the central controller regarding the physical characteristics of the disposable assembly when the disposable assembly is connected with the fluid pump.

14. The disposable assembly of claim 1 comprising a syringe substantially permanently attached to the needle hub, the pressure sensor and the identification circuit.

15. The disposable assembly of claim 1 comprising a needle permanently affixed to the needle hub, wherein the needle hub is substantially permanently connected with the tubing and the pressure sensor.

16. The disposable assembly of claim 1 wherein the needle hub comprises a connector for connecting a needle assembly to the needle hub.

17. The disposable assembly of claim 1 wherein the pressure sensor is an electronic pressure sensor configured to provide signals indicative of the fluid pressure in the fluid line.

18. The disposable assembly of claim 1 wherein the configuration signal comprises a signal operable by the central controller to control the fluid flow parameters of flow rate and pressure used with the disposable assembly when the disposable assembly is connected with the fluid pump.

19. The disposable assembly of 18 wherein the identification circuit is substantially permanently connected with the pressure sensor.

20. The disposable fluid flow assembly of claim 1, wherein the first use signal includes data identifying the number of cycles or length of time that the disposable needle assembly has been used.

21. The disposable assembly of claim 20 wherein the data line is configured so that the identification circuit receives signals from the central controller when the disposable assembly is connected with the fluid pump and wherein the identification circuit is configured to receive signal from the central controller regarding the number of cycles or the amount of time that the disposable assembly is used with the fluid pump and wherein the identification circuit is configured to store data regarding the number of cycles or the amount of time.

22. The disposable assembly of claim 21 wherein the identification circuit is configured to provide the use signal to the central controller when the disposable assembly is connected with the fluid pump and the use signal is configured so that the central controller limits operation of the fluid pump in response to the use signal.

23. The disposable assembly of claim 20 wherein the identification circuit is configured so that the content or information of the identification circuit can be altered by the central controller when the disposable connector is connected with the fluid pump.

24. The disposable assembly of claim 20 comprising a syringe fixedly connected with the pressure sensor and the identification circuit, wherein the configuration signal provides data to the central controller when the disposable assembly is connected with the fluid pump such that the fluid pump purges a pre-set quantity of fluid from the syringe.

25. The disposable assembly of claim 20 comprising an elongated handle, wherein the hub forms a portion of the elongated handle.

26. The disposable assembly of claim 25 wherein the handle is substantially rigid.

27. The disposable assembly of claim 20 comprising a syringe substantially permanently attached to the needle hub, the pressure sensor and the identification circuit.

28. The disposable assembly of claim 20 comprising a needle permanently affixed to the needle hub, wherein the needle hub is substantially permanently connected with the tubing and the pressure sensor.

29. The disposable assembly of claim 20 wherein the configuration signal comprises a signal operable by the central controller to control the fluid flow parameters of flow rate and pressure used with the disposable assembly when the disposable assembly is connected with the fluid pump.

30. The disposable assembly of claim 20 wherein the identification circuit is configured to provide a connection verification circuit verifying that the pressure sensor is electrically connected with the fluid pump when the disposable assembly is connected with the fluid pump.

31. A disposable fluid flow assembly for operation in connection with a fluid pump configured to provide a flow of fluid to the disposable fluid flow assembly, wherein the fluid pump comprises a central controller having a memory and the central controller is configured to control the flow of fluid in response to manual commands input via an input element, wherein the disposable fluid flow assembly comprises:
    an elongated flexible tube;
    a needle hub connected with the flexible tube, wherein the hub is configured for connecting a needle with the hub
    a pressure sensor for sensing fluid pressure, wherein the pressure sensor is connected with the tube or the hub; and
    an identification circuit connected with the pressure sensor wherein the identification is configured to provide a plurality of signals to the central controller of the fluid pump when the disposable needle assembly is connected with the fluid pump, wherein the plurality of signals, including:
    a configuration signal indicative of the physical characteristics of the disposable needle assembly;
    a verification signal indicative of the disposable needle assembly being cooperable with the fluid pump;
    a first use signal identifying the particular disposable needle assembly so that the central controller can detect whether the specific disposable needle assembly was previously used.

32. The disposable assembly of claim 31 comprising a data connector configured to provide a data connection between the identification circuit and the fluid pump.

\* \* \* \* \*